US008679798B2

United States Patent
Yampolskaya et al.

(10) Patent No.: US 8,679,798 B2
(45) Date of Patent: Mar. 25, 2014

(54) **METHOD FOR PRODUCING AN L-AMINO ACID USING A BACTERIUM OF THE *ENTEROBACTERIACEAE* FAMILY**

(75) Inventors: Tatyana Abramovna Yampolskaya, Moscow (RU); Natalia Viktorovna Stoynova, Moscow (RU); Natalia Sergeevna Eremina, Moscow (RU); Irina Borisovna Altman, Moscow (RU); Leonid Romanovich Ptitsyn, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 1038 days.

(21) Appl. No.: 12/202,479

(22) Filed: Sep. 2, 2008

(65) Prior Publication Data

US 2009/0162908 A1    Jun. 25, 2009

(30) Foreign Application Priority Data

Dec. 21, 2007    (RU) ................................ 2007147434

(51) Int. Cl.
*C12P 13/00*    (2006.01)
(52) U.S. Cl.
USPC ........................................................ 435/115
(58) Field of Classification Search
None
See application file for complete search history.

(56) References Cited

U.S. PATENT DOCUMENTS

| | | | |
|---|---|---|---|
| 5,661,012 A | 8/1997 | Sano et al. |
| 5,827,698 A | 10/1998 | Kikuchi et al. |
| 5,830,716 A | 11/1998 | Kojima et al. |
| 5,932,453 A | 8/1999 | Kikuchi et al. |
| 6,040,160 A | 3/2000 | Kojima et al. |
| 6,911,332 B2 | 6/2005 | Usuda et al. |
| 7,026,149 B2 | 4/2006 | Usuda et al. |
| 7,029,893 B2 | 4/2006 | Usuda et al. |
| 7,060,475 B2 | 6/2006 | Usuda et al. |
| 7,090,998 B2 | 8/2006 | Ishikawa et al. |
| 7,192,748 B2 | 3/2007 | Usuda et al. |
| 7,220,570 B2 | 5/2007 | Usuda et al. |
| 7,306,933 B2 | 12/2007 | Dien et al. |
| 8,048,661 B2 | 11/2011 | Burgard et al. |
| 2002/0155556 A1 | 10/2002 | Imaizumi et al. |
| 2002/0160461 A1 | 10/2002 | Nakai et al. |
| 2003/0219882 A1 | 11/2003 | Hara et al. |
| 2004/0229305 A1 | 11/2004 | Usuda et al. |
| 2004/0229321 A1 | 11/2004 | Savrasova et al. |
| 2004/0265956 A1 | 12/2004 | Takikawa et al. |
| 2005/0181488 A1 | 8/2005 | Akhverdian et al. |
| 2005/0214911 A1 | 9/2005 | Marchenko et al. |
| 2005/0233308 A1 | 10/2005 | Nishio et al. |
| 2006/0019355 A1 | 1/2006 | Ueda et al. |
| 2006/0019356 A1 | 1/2006 | Usuda et al. |
| 2006/0030010 A1 | 2/2006 | Usuda et al. |
| 2006/0030011 A1 | 2/2006 | Usuda et al. |
| 2006/0088919 A1 | 4/2006 | Rybak et al. |
| 2006/0115878 A1 | 6/2006 | Hara et al. |
| 2006/0141586 A1 | 6/2006 | Rybak et al. |
| 2006/0234356 A1 | 10/2006 | Usuda et al. |
| 2006/0234357 A1 | 10/2006 | Usuda et al. |
| 2006/0269975 A1 | 11/2006 | Pompejus et al. |
| 2007/0212764 A1 | 9/2007 | Ptitsyn et al. |
| 2007/0249017 A1 | 10/2007 | Usuda et al. |
| 2011/0201089 A1 | 8/2011 | Burgard et al. |
| 2011/0207189 A1 | 8/2011 | Burgard et al. |
| 2011/0212507 A1 | 9/2011 | Burgard et al. |

FOREIGN PATENT DOCUMENTS

| | | |
|---|---|---|
| EP | 1182259 | 2/2002 |
| EP | 1 253 195 A1 | 10/2002 |
| EP | 1352966 | 10/2003 |
| EP | 1 715 055 A2 | 10/2006 |
| EP | 1 715 055 A3 | 10/2006 |
| EP | 1 715 056 A1 | 10/2006 |
| JP | 2001-136991 A | 5/2001 |
| WO | WO02/14522 A1 | 2/2002 |
| WO | WO02/22829 A2 | 3/2002 |
| WO | WO2006/135075 A1 | 12/2006 |
| WO | WO2007/013695 A1 | 2/2007 |
| WO | WO2007/039532 A2 | 4/2007 |
| WO | WO2007/039532 A3 | 4/2007 |
| WO | WO2007/100009 A1 | 9/2007 |
| WO | WO2007/136133 A1 | 11/2007 |
| WO | WO2008/002053 A1 | 1/2008 |
| WO | WO2008/010565 A2 | 1/2008 |
| WO | WO2008/032757 A1 | 3/2008 |
| WO | WO2008/072761 A2 | 6/2008 |
| WO | WO2008/081959 A1 | 7/2008 |
| WO | WO2008/102861 A1 | 8/2008 |
| WO | WO2008/107277 A1 | 9/2008 |
| WO | WO2011/099006 | 8/2011 |

OTHER PUBLICATIONS

Blaschkowski, H. P., et al., "Routes of Flavodoxin and Ferredoxin Reduction in *Escherichia coli* CoA-Acylating Pyruvate: Flavodoxin and NADPH: Flavodoxin Oxidoreductases Participating in the Activation of Pyruvate Formate-Lyase," Eur. J. Chem. 1982;123:563-569.
Ferredoxin oxidoreductase beta subunit [*Methanococcus maripaludis* S2]., [online], GenBank, Jan. 18, 2006, accession:NP_988624.
Hypothetical protein, MMP1502 [*Methanococcus maripaludis* S2]., [online], GenBank, Jan. 18, 2006, accession:NP_988622.
Hypothetical protein, pyruvate oxidoreductase-associated [*Methanococcus maripaludis* S2]., [online], GenBank, Jan. 18, 2006, accession:NP_988623.
Ikeda, T., et al., "Anabolic five subunit-type pyruvate:ferredoxin oxidoreductase from *Hydrogenobacter thermophilus* TK-6," Biochem. Biophys. Res. Commun. 2006;340:76-82.
Indolepyruvate ferredoxin oxidoreductase [*Methanococcus maripaludis* S2]., [online], GenBank, Jan. 18, 2006, accession:NP_988627.
KEGG (Kyoto Encyclopedia of Genes and Genomes) Entry No. b1378.

(Continued)

*Primary Examiner* — Brian J Gangle
(74) *Attorney, Agent, or Firm* — Shelly Guest Cermak; Cermak Nakajima LLP

(57) ABSTRACT

The present invention provides a method for producing an L-amino acid from ethanol using a bacterium of the *Enterobacteriaceae* family, wherein the bacterium has been modified to enhance the expression of the ydbK gene.

4 Claims, 2 Drawing Sheets

(56) References Cited

OTHER PUBLICATIONS

Lin, W., et al., "The importance of *porE* and *porF* in the anabolic pyruvate oxidoreductase of *Methanococcus maripaludis*," Arch. Microbiol. 2004;181:68-73.

Lin, W. C., et al., "The anabolic pyruvate oxidoreductase from *Methanococcus maripaludis*," Arch. Microbiol. 2003;179:444-456.

Probable pyruvate-flavodoxin oxidoreductase., [online], Jul. 10, 2007, accession:P52647.

Pyruvate flavodoxin/ferrodoxin oxidoreductase [*Chlorobium tepidum* TLS]., [online], GenBank, Dec. 2, 2005, accession:NP_662511.

Pyruvate oxidoreductase (synthase) subunit alpha [*Methanococcus maripaludis* S2]., [online], GenBank, Jan. 18, 2006, accession:NP_988625.

Pyruvate oxidoreductase (synthase) subunit delta [*Methanococcus maripaludis* S2]., [online], GenBank, Jan. 18, 2006, accession:NP_988626.

Reed, J. L., et al., "An expanded genome-scale model of *Escherichia coli* K-12 (*i*JR904 GSM/GPR)," Genome Biology 2003;4:R54.

Rotte, C., et al., "PyruvateL NADP+ Oxidoreductase from the Mitochondrion of *Euglena gracilis* and from the Apicomplexan *Cryptosporidium parvum*: A Biochemical Relic Linking Pyruvate Metabolism in Mitochondriate and Amitochondriate Protists," Mol. Bio. Evol. 2001:18(5):710-720.

International Search Report for PCT Patent App. No. PCT/JP2008/065834 (Oct. 7, 2008).

Mahadevan, R., et al., "Characterization of Metabolism in the Fe(III)-Reducing Organism *Geobacter sulfurreducens* by Constraint-Based Modeling," Appl. Environmen. Microbiol. 2006;72(2):1558-1568.

Office Action from Chinese Patent App. No. 200880105639.9 (Aug. 22, 2012).

Pyruvate: NADP+ oxidoreductase [*Euglena gracilis*], [online], GenBank, Jul. 28, 2001, Accession No. BAB12024.1; retrieved Dec. 22, 2011.

Fused predicted pyruvate-flavodoxin oxidoreductase: conserved protein/conserved protein/FeS binding protein [*Escherichia coli* str. K-12 substr. MG1655], [online], GenBank, Nov. 18, 2011, Accession No. NP_415896.1; retrieved Dec. 22, 2011.

Office Action from Chinese Patent App. No. 200880105639.9 (Nov. 17, 2011).

Figure 1. The construction of the plasmid pPLydbK3.
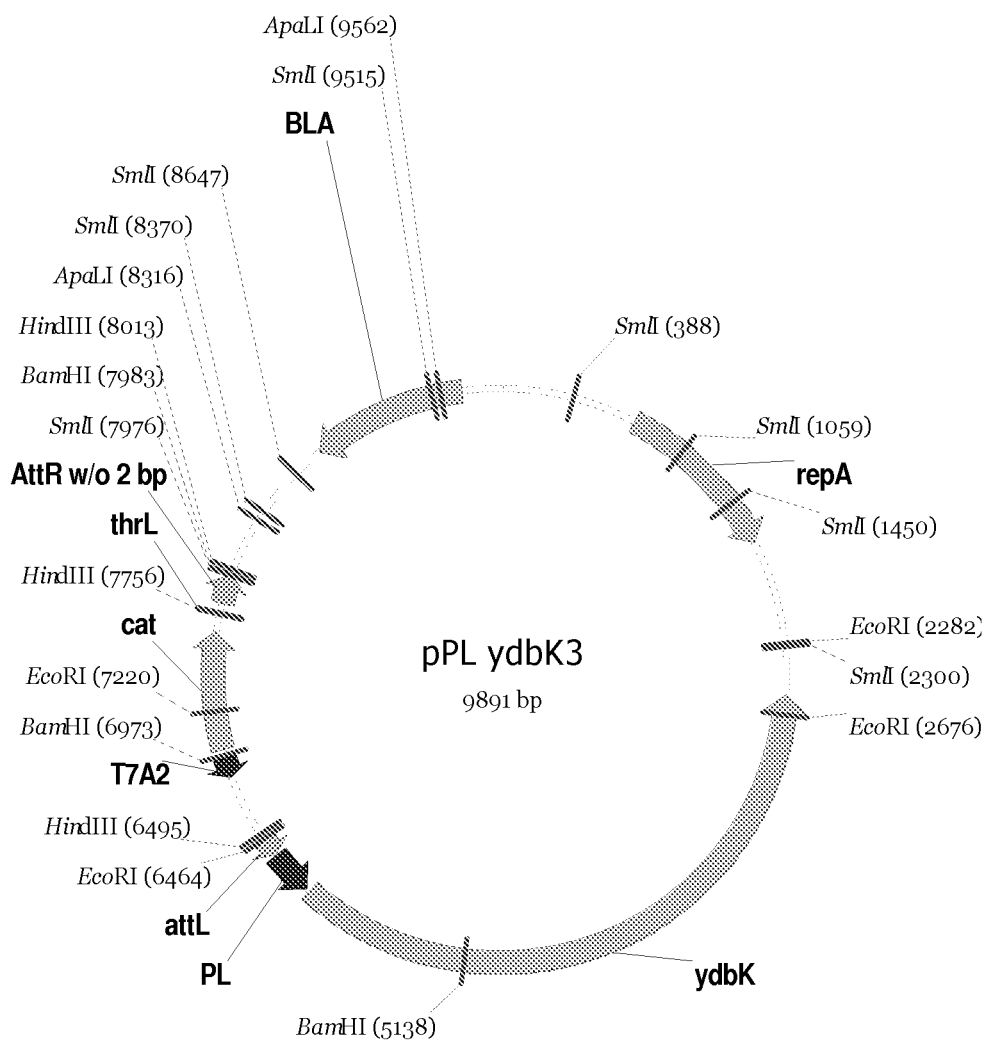

Figure 2. Effect of enhancing expression of the *ydbK* gene on the growth of *E.coli*.
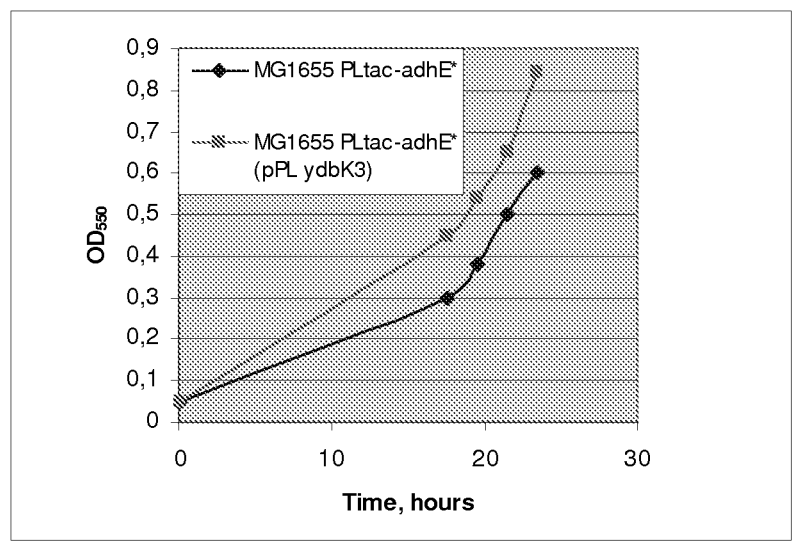

SEQUENCE LISTING

```
<160> NUMBER OF SEQ ID NOS: 20

<210> SEQ ID NO 1
<211> LENGTH: 3525
<212> TYPE: DNA
<213> ORGANISM: Escherichia coli
<220> FEATURE:
```

<221> NAME/KEY: CDS
<222> LOCATION: (1)..(3525)

<400> SEQUENCE: 1

| | | | | | | | | | | | | | | | | |
|---|---|---|---|---|---|---|---|---|---|---|---|---|---|---|---|---|
| atg | att | act | att | gac | ggt | aat | ggc | gcg | gtt | gct | tcg | gtc | gca | ttt | cgc | 48 |
| Met | Ile | Thr | Ile | Asp | Gly | Asn | Gly | Ala | Val | Ala | Ser | Val | Ala | Phe | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | agt | gaa | gtt | atc | gcc | atc | tac | cct | att | acc | ccc | agt | tcc | acg | atg | 96 |
| Thr | Ser | Glu | Val | Ile | Ala | Ile | Tyr | Pro | Ile | Thr | Pro | Ser | Ser | Thr | Met | |
| | | | 20 | | | | | 25 | | | | | 30 | | | |

| | | | | | | | | | | | | | | | | |
|---|---|---|---|---|---|---|---|---|---|---|---|---|---|---|---|---|
| gca | gaa | cag | gct | gat | gcc | tgg | gcc | gga | aac | ggc | tta | aag | aac | gtt | tgg | 144 |
| Ala | Glu | Gln | Ala | Asp | Ala | Trp | Ala | Gly | Asn | Gly | Leu | Lys | Asn | Val | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | gac | aca | cca | cgc | gtg | gtt | gaa | atg | cag | tcg | gaa | gcg | ggt | gct | atc | 192 |
| Gly | Asp | Thr | Pro | Arg | Val | Val | Glu | Met | Gln | Ser | Glu | Ala | Gly | Ala | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| gct | acc | gtg | cat | ggc | gct | ttg | cag | acg | ggt | gcc | ctt | tca | aca | tcg | ttt | 240 |
| Ala | Thr | Val | His | Gly | Ala | Leu | Gln | Thr | Gly | Ala | Leu | Ser | Thr | Ser | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| acg | tca | tcg | cag | ggt | ttg | ctg | ctg | atg | atc | ccg | acg | ctg | tac | aaa | ctg | 288 |
| Thr | Ser | Ser | Gln | Gly | Leu | Leu | Leu | Met | Ile | Pro | Thr | Leu | Tyr | Lys | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | ggc | gaa | cta | aca | ccg | ttt | gtc | ctg | cat | gta | gcg | gca | cgt | acc | gtt | 336 |
| Ala | Gly | Glu | Leu | Thr | Pro | Phe | Val | Leu | His | Val | Ala | Ala | Arg | Thr | Val | |
| | | | | 100 | | | | | 105 | | | | | 110 | | |

| | | | | | | | | | | | | | | | | |
|---|---|---|---|---|---|---|---|---|---|---|---|---|---|---|---|---|
| gcc | aca | cat | gca | ctc | tct | att | ttt | ggc | gat | cat | tcc | gac | gtt | atg | gcg | 384 |
| Ala | Thr | His | Ala | Leu | Ser | Ile | Phe | Gly | Asp | His | Ser | Asp | Val | Met | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| gtg | cgc | cag | acg | ggt | tgc | gcg | atg | ttg | tgt | gca | gca | aac | gtc | cag | gaa | 432 |
| Val | Arg | Gln | Thr | Gly | Cys | Ala | Met | Leu | Cys | Ala | Ala | Asn | Val | Gln | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| gcg | caa | gac | ttt | gct | ctc | att | tcg | caa | atc | gcg | acg | ctg | aaa | agc | cgc | 480 |
| Ala | Gln | Asp | Phe | Ala | Leu | Ile | Ser | Gln | Ile | Ala | Thr | Leu | Lys | Ser | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtg | cca | ttt | att | cat | ttc | ttt | gat | ggt | ttc | cgc | acg | tcc | cac | gaa | atc | 528 |
| Val | Pro | Phe | Ile | His | Phe | Phe | Asp | Gly | Phe | Arg | Thr | Ser | His | Glu | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | aaa | att | gtc | ccg | ctg | gcc | gat | gac | acg | att | ctt | gat | ctc | atg | ccg | 576 |
| Asn | Lys | Ile | Val | Pro | Leu | Ala | Asp | Asp | Thr | Ile | Leu | Asp | Leu | Met | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | gtc | gaa | att | gat | gct | cat | cgc | gcc | cgg | gca | ctc | aac | ccg | gaa | cat | 624 |
| Gln | Val | Glu | Ile | Asp | Ala | His | Arg | Ala | Arg | Ala | Leu | Asn | Pro | Glu | His | |
| | | 195 | | | | | 200 | | | | | 205 | | | | |

| | | | | | | | | | | | | | | | | |
|---|---|---|---|---|---|---|---|---|---|---|---|---|---|---|---|---|
| ccg | gtg | atc | cgc | ggt | acg | tcc | gcc | aat | cct | gac | act | tat | ttc | cag | tct | 672 |
| Pro | Val | Ile | Arg | Gly | Thr | Ser | Ala | Asn | Pro | Asp | Thr | Tyr | Phe | Gln | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| cgc | gaa | gcc | acc | aac | cca | tgg | tac | aac | gcg | gtc | tat | gac | cat | gtt | gaa | 720 |
| Arg | Glu | Ala | Thr | Asn | Pro | Trp | Tyr | Asn | Ala | Val | Tyr | Asp | His | Val | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cag | gcg | atg | aat | gat | ttc | tct | gcc | gcg | aca | ggt | cgt | cag | tat | cag | ccg | 768 |
| Gln | Ala | Met | Asn | Asp | Phe | Ser | Ala | Ala | Thr | Gly | Arg | Gln | Tyr | Gln | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| ttt | gaa | tat | tac | ggg | cat | ccg | caa | gcg | gaa | cgg | gtg | att | atc | ctg | atg | 816 |
| Phe | Glu | Tyr | Tyr | Gly | His | Pro | Gln | Ala | Glu | Arg | Val | Ile | Ile | Leu | Met | |
| | | | | 260 | | | | | 265 | | | | | 270 | | |

| | | | | | | | | | | | | | | | | |
|---|---|---|---|---|---|---|---|---|---|---|---|---|---|---|---|---|
| ggc | tct | gcc | att | ggc | acc | tgt | gaa | gaa | gtg | gtt | gat | gaa | ttg | cta | acc | 864 |
| Gly | Ser | Ala | Ile | Gly | Thr | Cys | Glu | Glu | Val | Val | Asp | Glu | Leu | Leu | Thr | |
| | | | | 275 | | | | | 280 | | | | | 285 | | |

| | | | | | | | | | | | | | | | | |
|---|---|---|---|---|---|---|---|---|---|---|---|---|---|---|---|---|
| cgt | ggc | gaa | aaa | gtt | ggc | gtg | ctg | aaa | gtt | cgc | ctg | tac | cgc | ccc | ttc | 912 |
| Arg | Gly | Glu | Lys | Val | Gly | Val | Leu | Lys | Val | Arg | Leu | Tyr | Arg | Pro | Phe | |
| | | | 290 | | | | | 295 | | | | | 300 | | | |

```
tcc gct aaa cat tta ctg caa gct ctg ccg gga tcc gta cgc agc gtg      960
Ser Ala Lys His Leu Leu Gln Ala Leu Pro Gly Ser Val Arg Ser Val
305                 310                 315                 320 gcg gta ctg gac aga acc aaa gaa ccc ggt gcc cag gca gaa ccg ctc     1008
Ala Val Leu Asp Arg Thr Lys Glu Pro Gly Ala Gln Ala Glu Pro Leu
                325                 330                 335 tat ctg gat gta atg acc gca ctg gca gaa gcc ttt aat aat ggc gag     1056
Tyr Leu Asp Val Met Thr Ala Leu Ala Glu Ala Phe Asn Asn Gly Glu
            340                 345                 350 cgc gaa act ctg ccc cgt gtc att ggt ggg cgc tat ggt ctt tca tcc     1104
Arg Glu Thr Leu Pro Arg Val Ile Gly Gly Arg Tyr Gly Leu Ser Ser
        355                 360                 365 aaa gaa ttt ggc cca gac tgt gta ctg gcg gta ttt gcc gag ctc aac     1152
Lys Glu Phe Gly Pro Asp Cys Val Leu Ala Val Phe Ala Glu Leu Asn
370                 375                 380 gcg gct aaa ccg aaa gcg cgc ttt acg gtt ggt att tac gat gat gtg     1200
Ala Ala Lys Pro Lys Ala Arg Phe Thr Val Gly Ile Tyr Asp Asp Val
385                 390                 395                 400 acc aat ctg tca ctg ccg ttg ccg gaa aac acc ctg cca aac tcg gcg     1248
Thr Asn Leu Ser Leu Pro Leu Pro Glu Asn Thr Leu Pro Asn Ser Ala
                405                 410                 415 aaa ctg gaa gcc ttg ttt tat ggc ctt ggt agt gat ggc agc gtt tcc     1296
Lys Leu Glu Ala Leu Phe Tyr Gly Leu Gly Ser Asp Gly Ser Val Ser
            420                 425                 430 gcg acc aaa aac aat atc aag att atc ggt aat tcc acg ccg tgg tac     1344
Ala Thr Lys Asn Asn Ile Lys Ile Ile Gly Asn Ser Thr Pro Trp Tyr
        435                 440                 445 gca cag ggc tat ttt gtt tac gac tcc aaa aag gcg ggc ggc ctg acg     1392
Ala Gln Gly Tyr Phe Val Tyr Asp Ser Lys Lys Ala Gly Gly Leu Thr
    450                 455                 460 gtt tct cac ctt cga gtg agc gaa cag ccg att cgt tcc gct tat ctc     1440
Val Ser His Leu Arg Val Ser Glu Gln Pro Ile Arg Ser Ala Tyr Leu
465                 470                 475                 480 att tcc cag gct gat ttt gtt ggc tgc cac cag ttg cag ttt atc gat     1488
Ile Ser Gln Ala Asp Phe Val Gly Cys His Gln Leu Gln Phe Ile Asp
                485                 490                 495 aaa tat cag atg gct gag cgt tta aaa cct ggc ggc att ttc ctg ctc     1536
Lys Tyr Gln Met Ala Glu Arg Leu Lys Pro Gly Gly Ile Phe Leu Leu
            500                 505                 510 aac acg ccg tac agc gca gat gaa gtg tgg tcg cgc ttg ccg caa gaa     1584
Asn Thr Pro Tyr Ser Ala Asp Glu Val Trp Ser Arg Leu Pro Gln Glu
        515                 520                 525 gtt cag gcc gtg tta aac cag aaa aaa gcg cgc ttc tat gtg att aac     1632
Val Gln Ala Val Leu Asn Gln Lys Lys Ala Arg Phe Tyr Val Ile Asn
    530                 535                 540 gcg gcg aaa atc gcc cgc gaa tgt ggc ctg gcg gcc cgt att aat acc     1680
Ala Ala Lys Ile Ala Arg Glu Cys Gly Leu Ala Ala Arg Ile Asn Thr
545                 550                 555                 560 gtc atg cag atg gct ttt ttc cat ctg acg caa att ctg cct ggc gat     1728
Val Met Gln Met Ala Phe Phe His Leu Thr Gln Ile Leu Pro Gly Asp
                565                 570                 575 agc gcc ctc gca gaa ttg cag ggt gcg att gcc aaa agt tac agt agc     1776
Ser Ala Leu Ala Glu Leu Gln Gly Ala Ile Ala Lys Ser Tyr Ser Ser
            580                 585                 590 aaa ggc cag gat ctg gtg gaa cgc aac tgg cag gct ctg gcg ctg gcg     1824
Lys Gly Gln Asp Leu Val Glu Arg Asn Trp Gln Ala Leu Ala Leu Ala
        595                 600                 605 cgt gaa tcc gta gaa gaa gtt ccg ttg caa ccg gta aat ccg cac agc     1872
Arg Glu Ser Val Glu Glu Val Pro Leu Gln Pro Val Asn Pro His Ser
    610                 615                 620
```

-continued

| | |
|---|---|
| gcc aat cga ccg cca gtg gtt tcc gat gcc gcc cct gat ttc gtg aaa<br>Ala Asn Arg Pro Pro Val Val Ser Asp Ala Ala Pro Asp Phe Val Lys<br>625                                  630                            635                            640 | 1920 |
| acc gta acc gct gcg atg ctc gcc ggg ctt ggt gac gcc ctc ccc gtt<br>Thr Val Thr Ala Ala Met Leu Ala Gly Leu Gly Asp Ala Leu Pro Val<br>                           645                            650                            655 | 1968 |
| tcg gcg ctg ccg cca gac ggc acc tgg ccg atg ggc act acg cgc tgg<br>Ser Ala Leu Pro Pro Asp Gly Thr Trp Pro Met Gly Thr Thr Arg Trp<br>          660                               665                            670 | 2016 |
| gaa aaa cgc aat atc gcc gaa gag atc ccc atc tgg aaa gag gaa ctc<br>Glu Lys Arg Asn Ile Ala Glu Glu Ile Pro Ile Trp Lys Glu Glu Leu<br>675                                  680                            685 | 2064 |
| tgt acc caa tgt aac cac tgc gtt gcc gct tgc cca cac tca gct att<br>Cys Thr Gln Cys Asn His Cys Val Ala Ala Cys Pro His Ser Ala Ile<br>690                                  695                            700 | 2112 |
| cgc gca aaa gtg gtg ccg cct gaa gcg atg gaa aac gcc cct gcc agc<br>Arg Ala Lys Val Val Pro Pro Glu Ala Met Glu Asn Ala Pro Ala Ser<br>705                                710                            715                        720 | 2160 |
| ctg cat tcg ctg gat gtg aaa tcg cgt gat atg cgc ggg cag aaa tat<br>Leu His Ser Leu Asp Val Lys Ser Arg Asp Met Arg Gly Gln Lys Tyr<br>                           725                            730                            735 | 2208 |
| gtc ttg cag gtg gca ccg gaa gat tgc acc ggt tgt aac ctg tgc gtc<br>Val Leu Gln Val Ala Pro Glu Asp Cys Thr Gly Cys Asn Leu Cys Val<br>                        740                            745                            750 | 2256 |
| gaa gtt tgc ccg gcg aaa gac cgt cag aat cca gag att aaa gcc atc<br>Glu Val Cys Pro Ala Lys Asp Arg Gln Asn Pro Glu Ile Lys Ala Ile<br>               755                            760                            765 | 2304 |
| aat atg atg tct cgc ctg gaa cat gtc gaa gaa gag aaa atc aat tac<br>Asn Met Met Ser Arg Leu Glu His Val Glu Glu Glu Lys Ile Asn Tyr<br>770                                  775                            780 | 2352 |
| gat ttc ttc ctc aac ctg cca gaa atc gac cgt agc aaa ctg gaa cgt<br>Asp Phe Phe Leu Asn Leu Pro Glu Ile Asp Arg Ser Lys Leu Glu Arg<br>785                                  790                            795                        800 | 2400 |
| att gat att cgt aca tcg cag ctg att aca ccg ctg ttt gaa tat tca<br>Ile Asp Ile Arg Thr Ser Gln Leu Ile Thr Pro Leu Phe Glu Tyr Ser<br>                           805                            810                            815 | 2448 |
| ggt gct tgc tcc ggt tgt ggc gag acg ccg tat att aaa tta ctg act<br>Gly Ala Cys Ser Gly Cys Gly Glu Thr Pro Tyr Ile Lys Leu Leu Thr<br>                        820                            825                            830 | 2496 |
| cag ctc tat ggc gac cgg atg ttg atc gct aac gcc act ggc tgt tct<br>Gln Leu Tyr Gly Asp Arg Met Leu Ile Ala Asn Ala Thr Gly Cys Ser<br>                       835                            840                            845 | 2544 |
| tca att tat ggc ggt aac ctg ccc tct aca ccg tat acc acc gat gcc<br>Ser Ile Tyr Gly Gly Asn Leu Pro Ser Thr Pro Tyr Thr Thr Asp Ala<br>850                                  855                            860 | 2592 |
| aac ggt cgt ggg ccg gca tgg gcg aac tct cta ttt gaa gat aat gcc<br>Asn Gly Arg Gly Pro Ala Trp Ala Asn Ser Leu Phe Glu Asp Asn Ala<br>865                                  870                            875                        880 | 2640 |
| gaa ttt ggc ctt ggt ttc cgc ctg acg gtc gat caa cac cgt gtc cgc<br>Glu Phe Gly Leu Gly Phe Arg Leu Thr Val Asp Gln His Arg Val Arg<br>                        885                            890                            895 | 2688 |
| gtg ctg cgt ctg ctg gat caa ttt gcc gat aaa atc ccg gcg gaa tta<br>Val Leu Arg Leu Leu Asp Gln Phe Ala Asp Lys Ile Pro Ala Glu Leu<br>                       900                            905                            910 | 2736 |
| ctg acg gcg ttg aaa tca gac gcc acg cca gag gtt cgt cgt gaa cag<br>Leu Thr Ala Leu Lys Ser Asp Ala Thr Pro Glu Val Arg Arg Glu Gln<br>                        915                            920                            925 | 2784 |
| gtt gca gct tta cgc cag caa ctc aac gat gtt gcc gaa gca cat gaa<br>Val Ala Ala Leu Arg Gln Gln Leu Asn Asp Val Ala Glu Ala His Glu<br>                       930                            935                            940 | 2832 |

```
ctg cta cgt gat gca gat gca ctg gtg gaa aaa tca atc tgg ctg att   2880
Leu Leu Arg Asp Ala Asp Ala Leu Val Glu Lys Ser Ile Trp Leu Ile
945                 950                 955                 960 ggt ggt gat ggc tgg gct tac gat atc ggc ttt ggc ggt ctg gat cat   2928
Gly Gly Asp Gly Trp Ala Tyr Asp Ile Gly Phe Gly Gly Leu Asp His
            965                 970                 975 gta ttg agt ttg acg gaa aac gtc aac att ctg gtg ctg gat acg caa   2976
Val Leu Ser Leu Thr Glu Asn Val Asn Ile Leu Val Leu Asp Thr Gln
        980                 985                 990 tgc tat tcc aac acc ggt ggt cag gcg tcg aaa gcg aca ccg ctg ggt   3024
Cys Tyr Ser Asn Thr Gly Gly Gln Ala Ser Lys Ala Thr Pro Leu Gly
    995                1000                1005 gca gta act aaa ttt ggc gag cac ggc aaa cgt aaa gcg cgt aaa       3069
Ala Val Thr Lys Phe Gly Glu His Gly Lys Arg Lys Ala Arg Lys
1010                1015                1020 gat ctt ggc gtc agt atg atg atg tac ggt cat gtt tat gtg gcg       3114
Asp Leu Gly Val Ser Met Met Met Tyr Gly His Val Tyr Val Ala
1025                1030                1035 cag att tct ctc ggc gcg cag ctg aac cag acg gtg aaa gcg att       3159
Gln Ile Ser Leu Gly Ala Gln Leu Asn Gln Thr Val Lys Ala Ile
1040                1045                1050 cag gaa gcg gaa gcg tat ccg ggg cca tcg ctg atc att gct tat       3204
Gln Glu Ala Glu Ala Tyr Pro Gly Pro Ser Leu Ile Ile Ala Tyr
1055                1060                1065 agc ccg tgt gaa gag cat ggt tac gat ctg gca ctc agc cac gac       3249
Ser Pro Cys Glu Glu His Gly Tyr Asp Leu Ala Leu Ser His Asp
1070                1075                1080 cag atg cgc caa ctc aca gct acc ggc ttc tgg cca cta tat cgc       3294
Gln Met Arg Gln Leu Thr Ala Thr Gly Phe Trp Pro Leu Tyr Arg
1085                1090                1095 ttt gat ccg cgt cgt gcc gat gaa ggc aaa ctg ccg ctg gcc ttg       3339
Phe Asp Pro Arg Arg Ala Asp Glu Gly Lys Leu Pro Leu Ala Leu
1100                1105                1110 gat tca cgc ccg ccg tca gaa gca ccg gaa gaa acg tta ctt cac       3384
Asp Ser Arg Pro Pro Ser Glu Ala Pro Glu Glu Thr Leu Leu His
1115                1120                1125 gag caa cgt ttc cgt cgg ctg aat tcg cag cag cca gaa gtg gca       3429
Glu Gln Arg Phe Arg Arg Leu Asn Ser Gln Gln Pro Glu Val Ala
1130                1135                1140 gaa cag tta tgg aaa gat gct gca gct gat ttg caa aaa cgc tat       3474
Glu Gln Leu Trp Lys Asp Ala Ala Ala Asp Leu Gln Lys Arg Tyr
1145                1150                1155 gac ttc ctg gca caa atg gcc gga aaa gcg gaa aaa agc aac acc       3519
Asp Phe Leu Ala Gln Met Ala Gly Lys Ala Glu Lys Ser Asn Thr
1160                1165                1170 gat taa                                                            3525
Asp

<210> SEQ ID NO 2
<211> LENGTH: 1174
<212> TYPE: PRT
<213> ORGANISM: Escherichia coli

<400> SEQUENCE: 2

Met Ile Thr Ile Asp Gly Asn Gly Ala Val Ala Ser Val Ala Phe Arg
1               5                   10                  15

Thr Ser Glu Val Ile Ala Ile Tyr Pro Ile Thr Pro Ser Ser Thr Met
            20                  25                  30

Ala Glu Gln Ala Asp Ala Trp Ala Gly Asn Gly Leu Lys Asn Val Trp
        35                  40                  45
```

-continued

Gly Asp Thr Pro Arg Val Val Glu Met Gln Ser Glu Ala Gly Ala Ile
        50                  55                  60

Ala Thr Val His Gly Ala Leu Gln Thr Gly Ala Leu Ser Thr Ser Phe
 65                  70                  75                  80

Thr Ser Ser Gln Gly Leu Leu Leu Met Ile Pro Thr Leu Tyr Lys Leu
                 85                  90                  95

Ala Gly Glu Leu Thr Pro Phe Val Leu His Val Ala Ala Arg Thr Val
                100                 105                 110

Ala Thr His Ala Leu Ser Ile Phe Gly Asp His Ser Asp Val Met Ala
                115                 120                 125

Val Arg Gln Thr Gly Cys Ala Met Leu Cys Ala Ala Asn Val Gln Glu
        130                 135                 140

Ala Gln Asp Phe Ala Leu Ile Ser Gln Ile Ala Thr Leu Lys Ser Arg
145                 150                 155                 160

Val Pro Phe Ile His Phe Phe Asp Gly Phe Arg Thr Ser His Glu Ile
                165                 170                 175

Asn Lys Ile Val Pro Leu Ala Asp Asp Thr Ile Leu Asp Leu Met Pro
                180                 185                 190

Gln Val Glu Ile Asp Ala His Arg Ala Arg Ala Leu Asn Pro Glu His
        195                 200                 205

Pro Val Ile Arg Gly Thr Ser Ala Asn Pro Asp Thr Tyr Phe Gln Ser
210                 215                 220

Arg Glu Ala Thr Asn Pro Trp Tyr Asn Ala Val Tyr Asp His Val Glu
225                 230                 235                 240

Gln Ala Met Asn Asp Phe Ser Ala Ala Thr Gly Arg Gln Tyr Gln Pro
                245                 250                 255

Phe Glu Tyr Tyr Gly His Pro Gln Ala Glu Arg Val Ile Ile Leu Met
                260                 265                 270

Gly Ser Ala Ile Gly Thr Cys Glu Glu Val Val Asp Glu Leu Leu Thr
        275                 280                 285

Arg Gly Glu Lys Val Gly Val Leu Lys Val Arg Leu Tyr Arg Pro Phe
290                 295                 300

Ser Ala Lys His Leu Leu Gln Ala Leu Pro Gly Ser Val Arg Ser Val
305                 310                 315                 320

Ala Val Leu Asp Arg Thr Lys Glu Pro Gly Ala Gln Ala Glu Pro Leu
                325                 330                 335

Tyr Leu Asp Val Met Thr Ala Leu Ala Glu Ala Phe Asn Asn Gly Glu
                340                 345                 350

Arg Glu Thr Leu Pro Arg Val Ile Gly Gly Arg Tyr Gly Leu Ser Ser
        355                 360                 365

Lys Glu Phe Gly Pro Asp Cys Val Leu Ala Val Phe Ala Glu Leu Asn
370                 375                 380

Ala Ala Lys Pro Lys Ala Arg Phe Thr Val Gly Ile Tyr Asp Asp Val
385                 390                 395                 400

Thr Asn Leu Ser Leu Pro Leu Pro Glu Asn Thr Leu Pro Asn Ser Ala
                405                 410                 415

Lys Leu Glu Ala Leu Phe Tyr Gly Leu Gly Ser Asp Gly Ser Val Ser
                420                 425                 430

Ala Thr Lys Asn Asn Ile Lys Ile Ile Gly Asn Ser Thr Pro Trp Tyr
        435                 440                 445

Ala Gln Gly Tyr Phe Val Tyr Asp Ser Lys Lys Ala Gly Gly Leu Thr
450                 455                 460

Val Ser His Leu Arg Val Ser Glu Gln Pro Ile Arg Ser Ala Tyr Leu

```
                465                 470                 475                 480
Ile Ser Gln Ala Asp Phe Val Gly Cys His Gln Leu Gln Phe Ile Asp
                    485                 490                 495
Lys Tyr Gln Met Ala Glu Arg Leu Lys Pro Gly Gly Ile Phe Leu Leu
                    500                 505                 510
Asn Thr Pro Tyr Ser Ala Asp Glu Val Trp Ser Arg Leu Pro Gln Glu
                    515                 520                 525
Val Gln Ala Val Leu Asn Gln Lys Lys Ala Arg Phe Tyr Val Ile Asn
                530                 535                 540
Ala Ala Lys Ile Ala Arg Glu Cys Gly Leu Ala Ala Arg Ile Asn Thr
545                 550                 555                 560
Val Met Gln Met Ala Phe Phe His Leu Thr Gln Ile Leu Pro Gly Asp
                    565                 570                 575
Ser Ala Leu Ala Glu Leu Gln Gly Ala Ile Ala Lys Ser Tyr Ser Ser
                    580                 585                 590
Lys Gly Gln Asp Leu Val Glu Arg Asn Trp Gln Ala Leu Ala Leu Ala
                    595                 600                 605
Arg Glu Ser Val Glu Glu Val Pro Leu Gln Pro Val Asn Pro His Ser
                610                 615                 620
Ala Asn Arg Pro Pro Val Val Ser Asp Ala Ala Pro Asp Phe Val Lys
625                 630                 635                 640
Thr Val Thr Ala Ala Met Leu Ala Gly Leu Gly Asp Ala Leu Pro Val
                    645                 650                 655
Ser Ala Leu Pro Pro Asp Gly Thr Trp Pro Met Gly Thr Thr Arg Trp
                    660                 665                 670
Glu Lys Arg Asn Ile Ala Glu Ile Pro Ile Trp Lys Glu Glu Leu
                    675                 680                 685
Cys Thr Gln Cys Asn His Cys Val Ala Ala Cys Pro His Ser Ala Ile
                690                 695                 700
Arg Ala Lys Val Val Pro Pro Glu Ala Met Glu Asn Ala Pro Ala Ser
705                 710                 715                 720
Leu His Ser Leu Asp Val Lys Ser Arg Asp Met Arg Gly Gln Lys Tyr
                    725                 730                 735
Val Leu Gln Val Ala Pro Glu Asp Cys Thr Gly Cys Asn Leu Cys Val
                    740                 745                 750
Glu Val Cys Pro Ala Lys Asp Arg Gln Asn Pro Glu Ile Lys Ala Ile
                755                 760                 765
Asn Met Met Ser Arg Leu Glu His Val Glu Glu Lys Ile Asn Tyr
770                 775                 780
Asp Phe Phe Leu Asn Leu Pro Glu Ile Asp Arg Ser Lys Leu Glu Arg
785                 790                 795                 800
Ile Asp Ile Arg Thr Ser Gln Leu Ile Thr Pro Leu Phe Glu Tyr Ser
                    805                 810                 815
Gly Ala Cys Ser Gly Cys Gly Glu Thr Pro Tyr Ile Lys Leu Leu Thr
                    820                 825                 830
Gln Leu Tyr Gly Asp Arg Met Leu Ile Ala Asn Ala Thr Gly Cys Ser
                    835                 840                 845
Ser Ile Tyr Gly Gly Asn Leu Pro Ser Thr Pro Tyr Thr Thr Asp Ala
                850                 855                 860
Asn Gly Arg Gly Pro Ala Trp Ala Asn Ser Leu Phe Glu Asp Asn Ala
865                 870                 875                 880
Glu Phe Gly Leu Gly Phe Arg Leu Thr Val Asp Gln His Arg Val Arg
                    885                 890                 895
```

-continued

Val Leu Arg Leu Leu Asp Gln Phe Ala Asp Lys Ile Pro Ala Glu Leu
            900                 905                 910

Leu Thr Ala Leu Lys Ser Asp Ala Thr Pro Glu Val Arg Glu Gln
        915                 920                 925

Val Ala Ala Leu Arg Gln Gln Leu Asn Asp Val Ala Glu Ala His Glu
    930                 935                 940

Leu Leu Arg Asp Ala Asp Ala Leu Val Glu Lys Ser Ile Trp Leu Ile
945                 950                 955                 960

Gly Gly Asp Gly Trp Ala Tyr Asp Ile Gly Phe Gly Gly Leu Asp His
                965                 970                 975

Val Leu Ser Leu Thr Glu Asn Val Asn Ile Leu Val Leu Asp Thr Gln
            980                 985                 990

Cys Tyr Ser Asn Thr Gly Gly Gln Ala Ser Lys Ala Thr Pro Leu Gly
        995                 1000                1005

Ala Val Thr Lys Phe Gly Glu His Gly Lys Arg Lys Ala Arg Lys
    1010                1015                1020

Asp Leu Gly Val Ser Met Met Met Tyr Gly His Val Tyr Val Ala
    1025                1030                1035

Gln Ile Ser Leu Gly Ala Gln Leu Asn Gln Thr Val Lys Ala Ile
    1040                1045                1050

Gln Glu Ala Glu Ala Tyr Pro Gly Pro Ser Leu Ile Ile Ala Tyr
    1055                1060                1065

Ser Pro Cys Glu Glu His Gly Tyr Asp Leu Ala Leu Ser His Asp
    1070                1075                1080

Gln Met Arg Gln Leu Thr Ala Thr Gly Phe Trp Pro Leu Tyr Arg
    1085                1090                1095

Phe Asp Pro Arg Arg Ala Asp Glu Gly Lys Leu Pro Leu Ala Leu
    1100                1105                1110

Asp Ser Arg Pro Pro Ser Glu Ala Pro Glu Glu Thr Leu Leu His
    1115                1120                1125

Glu Gln Arg Phe Arg Arg Leu Asn Ser Gln Gln Pro Glu Val Ala
    1130                1135                1140

Glu Gln Leu Trp Lys Asp Ala Ala Ala Asp Leu Gln Lys Arg Tyr
    1145                1150                1155

Asp Phe Leu Ala Gln Met Ala Gly Lys Ala Glu Lys Ser Asn Thr
    1160                1165                1170

Asp

<210> SEQ ID NO 3
<211> LENGTH: 70
<212> TYPE: DNA
<213> ORGANISM: Artificial sequence
<220> FEATURE:
<223> OTHER INFORMATION: primer P1

<400> SEQUENCE: 3
gatgaaagcg ttatccaaac tgaaagcgga agaggccgac gcactttgcg ccgaataaat        60
acctgtgacg                                                               70

<210> SEQ ID NO 4
<211> LENGTH: 69
<212> TYPE: DNA
<213> ORGANISM: Artificial sequence
<220> FEATURE:
<223> OTHER INFORMATION: primer P2

<400> SEQUENCE: 4

```
ttaatcccag ctcagaataa ctttcccgga ctttacgccc cgccctgcca ctcatcgcag    60
tactgttgt                                                            69
```

<210> SEQ ID NO 5
<211> LENGTH: 18
<212> TYPE: DNA
<213> ORGANISM: Artificial sequence
<220> FEATURE:
<223> OTHER INFORMATION: primer P3

<400> SEQUENCE: 5

```
cggtcatgct tggtgatg                                                  18
```

<210> SEQ ID NO 6
<211> LENGTH: 21
<212> TYPE: DNA
<213> ORGANISM: Artificial sequence
<220> FEATURE:
<223> OTHER INFORMATION: primer P4

<400> SEQUENCE: 6

```
ttaatcccag ctcagaataa c                                              21
```

<210> SEQ ID NO 7
<211> LENGTH: 183
<212> TYPE: DNA
<213> ORGANISM: Artificial sequence
<220> FEATURE:
<223> OTHER INFORMATION: hybrid promoter

<400> SEQUENCE: 7

```
ctagatctct cacctaccaa acaatgcccc cctgcaaaaa ataaattcat aaaaaacata    60
cagataacca tctgcggtga taaattatct ctggcggtgt tgacaattaa tcatcggctc   120
gtataatgtg tggaattgtg agcggtttaa cattatcagg agagcattat ggctgttact   180
aat                                                                 183
```

<210> SEQ ID NO 8
<211> LENGTH: 69
<212> TYPE: DNA
<213> ORGANISM: Artificial sequence
<220> FEATURE:
<223> OTHER INFORMATION: primer P5

<400> SEQUENCE: 8

```
cgttattgtt atctagttgt gcaaaacatg ctaatgtagc attacgcccc gccctgccac    60
tcatcgcag                                                            69
```

<210> SEQ ID NO 9
<211> LENGTH: 58
<212> TYPE: DNA
<213> ORGANISM: Artificial sequence
<220> FEATURE:
<223> OTHER INFORMATION: primer P6

<400> SEQUENCE: 9

```
attagtaaca gccataatgc tctcctgata atgttaaacc gctcacaatt ccacacat      58
```

<210> SEQ ID NO 10
<211> LENGTH: 24
<212> TYPE: DNA
<213> ORGANISM: Artificial sequence
<220> FEATURE:
<223> OTHER INFORMATION: primer P7

```
<400> SEQUENCE: 10
acttgttctt gagtgaaact ggca                                               24

<210> SEQ ID NO 11
<211> LENGTH: 22
<212> TYPE: DNA
<213> ORGANISM: Artificial sequence
<220> FEATURE:
<223> OTHER INFORMATION: primer P8

<400> SEQUENCE: 11
aagacgcgct gacaatacgc ct                                                 22

<210> SEQ ID NO 12
<211> LENGTH: 69
<212> TYPE: DNA
<213> ORGANISM: Artificial sequence
<220> FEATURE:
<223> OTHER INFORMATION: primer P9

<400> SEQUENCE: 12
cgttattgtt atctagttgt gcaaaacatg ctaatgtagc atcagaaaaa ctcatcgagc        60
atcaaatga                                                                69

<210> SEQ ID NO 13
<211> LENGTH: 65
<212> TYPE: DNA
<213> ORGANISM: Artificial sequence
<220> FEATURE:
<223> OTHER INFORMATION: primer P10

<400> SEQUENCE: 13
agccggagca gcttctttct tcgctgcagt ttcaccttct acgttgtgtc tcaaaatctc        60
tgatg                                                                    65

<210> SEQ ID NO 14
<211> LENGTH: 24
<212> TYPE: DNA
<213> ORGANISM: Artificial sequence
<220> FEATURE:
<223> OTHER INFORMATION: primer P11

<400> SEQUENCE: 14
aagacgcgct gacaatacgc cttt                                               24

<210> SEQ ID NO 15
<211> LENGTH: 24
<212> TYPE: DNA
<213> ORGANISM: Artificial sequence
<220> FEATURE:
<223> OTHER INFORMATION: primer P12

<400> SEQUENCE: 15
aaggggccgt ttatgttgcc agac                                               24

<210> SEQ ID NO 16
<211> LENGTH: 69
<212> TYPE: DNA
<213> ORGANISM: Artificial sequence
<220> FEATURE:
<223> OTHER INFORMATION: primer P13

<400> SEQUENCE: 16
catgtgggtt atgtacgaac atccggaaac tcacttcgaa aagtcggcgc tgcgctttat        60
```

```
ggatatccg                                                              69

<210> SEQ ID NO 17
<211> LENGTH: 64
<212> TYPE: DNA
<213> ORGANISM: Artificial sequence
<220> FEATURE:
<223> OTHER INFORMATION: oligonucleotide ydbK-attR

<400> SEQUENCE: 17
caaaagcgaa aatgcagaag aaagccattt gctaaacgct caagttagta taaaaaagct      60
gaac                                                                   64

<210> SEQ ID NO 18
<211> LENGTH: 64
<212> TYPE: DNA
<213> ORGANISM: Artificial sequence
<220> FEATURE:
<223> OTHER INFORMATION: oligonucleotide PL-ydbK

<400> SEQUENCE: 18
aagcaaccgc gccattaccg tcaatagtaa tcatatagct gtttccttct agacggccaa      60
tgct                                                                   64

<210> SEQ ID NO 19
<211> LENGTH: 21
<212> TYPE: DNA
<213> ORGANISM: Artificial sequence
<220> FEATURE:
<223> OTHER INFORMATION: oligonucleotide ydbKC1

<400> SEQUENCE: 19
cttcctctga tcttcaagcc a                                                21

<210> SEQ ID NO 20
<211> LENGTH: 20
<212> TYPE: DNA
<213> ORGANISM: Artificial sequence
<220> FEATURE:
<223> OTHER INFORMATION: oligonucleotide ydbK CH2

<400> SEQUENCE: 20
ttctgccatc gtggaactgg                                                  20
```

US 8,679,798 B2

METHOD FOR PRODUCING AN L-AMINO ACID USING A BACTERIUM OF THE *ENTEROBACTERIACEAE* FAMILY

BACKGROUND OF THE INVENTION

This application claims priority under 35 U.S.C. §119 to Russian Patent Application No. 2007147434, filed Dec. 21, 2007, which is incorporated by reference. The Sequence Listing in electronic format filed herewith is also hereby incorporated by reference in its entirety (File Name: US-371_Seq_List_Copy_1; File Size: 31 KB; Date Created: Sep. 2, 2008).

TECHNICAL FIELD

The present invention relates to the microbiological industry, and specifically to a method for producing an L-amino acid from ethanol using a bacterium of the *Enterobacteriaceae* family which has been modified to enhance the expression of the ydbK gene.

BACKGROUND ART

Conventionally, L-amino acids are industrially produced by fermentation methods utilizing strains of microorganisms obtained from natural sources, or mutants thereof. Typically, the microorganisms are modified to enhance production yields of L-amino acids.

Many techniques have been reported to enhance L-amino acid production yields, including transformation of microorganisms with recombinant DNA (U.S. Pat. No. 4,278,765). Other techniques for enhancing production yields include increasing the activities of enzymes involved in amino acid biosynthesis and/or desensitizing the target enzymes to feedback inhibition by the resulting L-amino acid (U.S. Pat. Nos. 4,346,170, 5,661,012 and 6,040,160).

YdbK is an uncharacterized protein. Based on sequence similarity, YdbK is predicted to be a pyruvate synthase (Reed J. L. et al, Genome Biology, 4(9):R54).

But currently, there have been no reports of enhancing expression of the ydbK gene for the purpose of producing L-amino acids.

SUMMARY OF THE INVENTION

Aspects of the present invention include enhancing the productivity of L-amino acid-producing strains and providing a method for producing non-aromatic or aromatic L-amino acids using these strains.

The above aspects were achieved by finding that enhancing expression of the ydbK gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the *Enterobacteriaceae* family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the *Enterobacteriaceae* family, wherein said bacterium has been modified to enhance the expression of the ydbK gene.

It is a further aspect of the present invention to provide the bacterium as described above, wherein said expression is enhanced by modifying an expression control sequence of the ydbK gene or by increasing the copy number of the ydbK gene.

It is a further aspect of the present invention to provide the bacterium as described above, wherein said bacterium belongs to the genus *Escherichia*.

It is a further aspect of the present invention to provide the bacterium as described above, wherein said bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide the bacterium as described above, wherein said non-aromatic L-amino acid is selected from the group consisting of L-threonine and L-valine.

It is a further aspect of the present invention to provide a method for producing an L-amino acid comprising:

cultivating the bacterium as described above in a medium containing ethanol as the sole carbon source, and collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide the method as described above, wherein said non-aromatic L-amino acid is selected from the group consisting of L-threonine and L-valine.

BRIEF DESCRIPTION OF THE DRAWINGS

FIG. 1 shows the construction of the plasmid pPLydbK3.

FIG. 2 shows the effect of enhancing the expression of the ydbK gene on the growth of *E. coli*.

DETAILED DESCRIPTION OF THE PREFERRED EMBODIMENTS

1. Bacterium

The bacterium is an L-amino acid-producing bacterium of the *Enterobacteriaceae* family, wherein the bacterium has been modified to enhance expression of the ydbK gene.

"L-amino acid-producing bacterium" means a bacterium which has an ability to produce and excrete or secrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of the bacterium, for example, *E. coli*, such as *E. coli* K-12, and preferably means that the bacterium is able to produce the target L-amino acid in the medium in an amount not less than 0.5 g/L, more preferably not less than 1.0 g/L. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The *Enterobacteriaceae* family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, bacteria classified as *Enterobacteriaceae* according to the taxonomy used by the NCBI (National Center for Biotechnology Information) database can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. An example of a bacterium belonging to the genus *Escherichia* is *Escherichia coli* (*E. coli*).

The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) may be used.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "enhancing the expression of the gene" means that the expression of the gene is increased as compared to that of a non-modified strain, for example, a wild-type strain. Examples of modifications include increasing the copy number of the expressed gene per cell, increasing the expression level of the gene, and so forth. The quantity of the copy number of the expressed gene is measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. Furthermore, wild-type strains that can be used as a control include, for example, *Escherichia coli* K-12 or *Pantoea ananatis* FERM BP-6614.

The ydbK gene (synonyms: ECK1374, b1378) encodes the YdbK protein, which is a putative pyruvate synthase (synonym B1378). The ydbK gene (nucleotides complementary to nucleotides at positions from 1,435,284 to 1,438,808; GenBank accession no. NC_000913.2; gi: 49175990) is located between the micC gene and the ydbJ ORF on the chromosome of *E. coli* K-12. The nucleotide sequence of the ydbK gene and the amino acid sequence of YdbK encoded by the ydbK gene are shown in SEQ ID NO: 1 and SEQ ID NO: 2, respectively.

Since there may be some differences in DNA sequences between the genera or strains of the *Enterobacteriaceae* family, the ydbK gene is not limited to the gene shown in SEQ ID No:1, but may include genes homologous to SEQ ID No:1. Therefore, the protein variant encoded by the ydbK gene may have a homology of not less than 80%, preferably not less than 90%, and most preferably not less than 95%, with respect to the entire amino acid sequence shown in SEQ ID NO. 2, as long as the activity of the YdbK protein is maintained. The phrase "protein variant" means proteins which have changes in the sequences, whether they are deletions, insertions, additions, or substitutions of amino acids. The number of changes in the variant proteins depends on the position in the three dimensional structure of the protein or the type of amino acid residues which are different. It may be 1 to 30, preferably 1 to 15, and more preferably 1 to 5 in SEQ ID NO: 2. These changes occur in regions of the protein which are not critical for the three dimensional structure of the protein. This is because some amino acids have high homology to one another so the three dimensional structure is not affected by such a change.

Homology between two amino acid sequences can be determined using well-known methods, for example, the computer program BLAST 2.0, which calculates three parameters: score, identity and similarity.

The substitution, deletion, insertion or addition of one or several amino acid residues may be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Therefore, the ydbK gene may be a variant which hybridizes under stringent conditions with the nucleotide sequence shown in SEQ ID NO: 1, or a probe which can be prepared from the nucleotide sequence, provided that it encodes a functional YdbK protein. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. The duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected depending on the hybridization conditions, and is usually 100 bp to 1 kbp.

Methods of enhancing gene expression include increasing the gene copy number. Introducing a gene into a vector that is able to function in a bacterium of the *Enterobacteriaceae* family increases the copy number of the gene. Preferably, low copy vectors are used. Examples of low-copy vectors include but are not limited to pSC101, pMW118, pMW119, and the like. The term "low copy vector" indicates vectors which are present in an amount of up to 5 copies per cell.

Enhancing gene expression may also be achieved by introducing multiple copies of the gene into the bacterial chromosome by, for example, homologous recombination, Mu integration, or the like. For example, one act of Mu integration allows for the introduction of up to 3 copies of the gene into the bacterial chromosome.

The copy number of a gene can also be increased by introducing multiple copies of the gene into the chromosomal DNA of the bacterium by, for example, homologous recombination using a target sequence which is present in multiple copies on the chromosomal DNA. Sequences having multiple copies on the chromosomal DNA include, but are not limited to repetitive DNA, or inverted repeats which are present at the end of a transposable element. Also, it is possible to incorporate the gene into a transposon, and allow it to be transferred to introduce multiple copies of the gene into the chromosomal DNA.

Enhancing gene expression may also be achieved by placing the DNA of the present invention under the control of a strong promoter. For example, the lac promoter, the trp promoter, the trc promoter, the $P_R$, or the $P_L$ promoters of lambda phage are all known to be strong promoters. The use of a strong promoter can be combined with multiplication of gene copies.

Alternatively, the effect of a promoter can be enhanced by, for example, introducing a mutation into the promoter to increase the transcription level of a gene located downstream from the promoter. Furthermore, it is known that by substituting several nucleotides in the spacer region between the ribosome binding site (RBS) and the start codon, especially the sequences immediately upstream of the start codon, the mRNA translatability is profoundly affected. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984).

Moreover, a nucleotide substitution can be introduced into the promoter region of a gene on the bacterial chromosome, which results in stronger promoter function. The expression control sequence can be altered, for example, in the same manner as the gene substitution using a temperature-sensitive plasmid, as disclosed in WO 00/18935 and JP 1-215280 A.

Methods for preparation of plasmid DNA, digestion and ligation of DNA, transformation, selection of an oligonucleotide as a primer, and the like, may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

Bacteria which are able to produce either an aromatic or a non-aromatic L-amino acid may be used. The bacterium can be obtained by enhancing expression of the ydbK gene in a bacterium which inherently has the ability to produce L-amino acids. Alternatively, the bacterium of present invention can be obtained by imparting the ability to produce L-amino acids to a bacterium which already has enhanced expression of the ydbK gene.

L-Threonine-Producing Bacteria

Examples of parent strains which can be used to derive L-threonine-producing bacteria include, but are not limited to, strains belonging to the genus *Escherichia*, such as *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939, 307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains the plasmid pVIC40 which was obtained by inserting a thrA*BC operon, which includes a mutant thrA gene, into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (Russia, 117545 Moscow, 1 Dorozhny proezd, 1) on Apr. 7, 1987 under the accession number VKPM B-3996.

*E. coli* VKPM B-5318 (EP 0593792B) may also be used to derive L-threonine-producing bacteria. The B-5318 strain is prototrophic with regard to isoleucine, and a temperature-sensitive lambda-phage C1 repressor and PR promoter replaces the regulatory region of the threonine operon in the pVIC40 plasmid. The VKPM B-5318 strain was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feedback inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes *Escherichia coli* aspartokinase homoserine dehydrogenase I has been elucidated (nucleotide positions 337 to 2799, GenBank accession no.NC_000913.2, gi: 49175990). The thrA gene is located between the thrL and thrB genes on the *E. coli* K-12 chromosome. The thrB gene which encodes *Escherichia coli* homoserine kinase has been elucidated (nucleotide positions 2801 to 3733, GenBank accession no.NC_000913.2, gi: 49175990). The thrB gene is located between the thrA and thrC genes on the *E. coli* K-12 chromosome. The thrC gene which encodes *Escherichia coli* threonine synthase has been elucidated (nucleotide positions 3734 to 5020, GenBank accession no.NC_000913.2, gi: 49175990). The thrC gene is located between the thrB gene and the yaaX open reading frame on the *E. coli* K-12 chromosome. All three genes function as a single threonine operon. To enhance expression of the threonine operon, the attenuator region which affects transcription can be removed from the operon (WO2005/049808, WO2003/097839).

The mutant thrA gene which codes for aspartokinase homoserine dehydrogenase I resistant to feedback inhibition by threonine, as well as the thrB and thrC genes can be obtained as one operon from the well-known pVIC40 plasmid, which is present in the threonine producing *E. coli* strain VKPM B-3996. pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to the ORF1 (ybiF gene, nucleotide positions 764 to 1651, GenBank accession number AAA218541, gi:440181) and is located between the pexB and ompX genes. The sequence expressing the protein encoded by the ORF1 has been designated the rhtA gene (rht: resistance to homoserine and threonine). Also, the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The *E. coli* asd gene has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes from other microorganisms can be obtained in a similar manner.

Also, the *E. coli* aspC gene has already been elucidated (nucleotide positions 983742 to 984932, GenBank accession no. NC_000913.1, gi:16128895), and can be obtained by PCR. The aspC genes from other microorganisms can be obtained in a similar manner.

L-Lysine-Producing Bacteria

Examples of L-lysine-producing *Escherichia* bacteria include mutants which are resistant to L-lysine analogues. L-lysine analogues inhibit growth of the bacteria, but this inhibition is fully or partially desensitized when L-lysine is present in the medium. Examples of the L-lysine analogues include, but are not limited to, oxalysine, lysine hydroxamate, S-(2-aminoethyl)-L-cysteine (AEC), γ-methyllysine, α-chlorocaprolactam, and so forth. Mutants which are resistant to these lysine analogues can be obtained by subjecting bacteria to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC196 strain is an L-lysine producing *Escherichia coli* bacterium. This bacterial strain was bred by conferring AEC resistance to the W3110 strain, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression is increased of one or more genes encoding an L-lysine biosynthetic enzyme. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenease (asd), and aspartase (aspA) (EP 1253195 A). In addition, the chosen parent strains may overexpress the cyo gene, which is involved in energy efficiency (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria also include strains with decreased or no activity of an enzyme that catalyzes a reaction which produces a compound other than L-lysine via a biosynthetic pathway which branches off from the biosynthetic pathway of L-lysine. Examples of these enzymes include homoserine dehydrogenase, lysine decarboxylase (U.S. Pat. No. 5,827,698), and the malic enzyme (WO2005/010175).

L-Cysteine-Producing Bacteria

Examples of parent strains which can be used to derive L-cysteine-producing bacteria include, but are not limited to, strains belonging to the genus *Escherichia*, such as *E. coli* JM15 which is transformed with different cysE alleles encoding feedback-resistant serine acetyltransferases (U.S. Pat. No. 6,218,168, Russian patent application 2003121601), *E. coli* W3110 with overexpressed genes which encode proteins which promote secretion of substances toxic to cells (U.S. Pat. No. 5,972,663), *E. coli* strains with reduced cysteine desulfohydrase activity (JP11155571A2), *E. coli* W3110 with increased activity of a positive transcriptional regulator for cysteine regulon encoded by the cysB gene (WO0127307A1), and the like.

L-Leucine-Producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A), *E. coli* strains obtained by the gene engineering method described in WO96/06926, *E. coli* H-9068 (JP 8-70879 A), and the like.

The chosen bacterium may also be improved by enhancing the expression of one or more genes which encode proteins involved in L-leucine biosynthesis. Examples include genes of the leuABCD operon, such as a mutant leuA gene coding for isopropylmalate synthase which is not subject to feedback inhibition by L-leucine (U.S. Pat. No. 6,403,342). In addition, the bacterium may be improved by enhancing the expression of one or more genes encoding proteins which promote secretion of L-amino acids from the bacterial cell. Examples of such genes include b2682 and b2683 (ygaZH genes) (EP 1239041 A2).

L-Histidine-Producing Bacteria

Examples of parent strains which can be used to derive L-histidine-producing bacteria include, but are not limited to, strains belonging to the genus *Escherichia*, such as *E. coli* strain 24 (VKPM B-5945, RU2003677) *E. coli* strain 80 (VKPM B-7270, RU2119536) *E. coli* NRRL B-12116-B12121 (U.S. Pat. No. 4,388,405) *E. coli* H-9342 (FERM BP-6675) and H-9343 (FERM BP-6676) (U.S. Pat. No. 6,344,347) *E. coli* H-9341 (FERM BP-6674) (EP1085087) *E. coli* AI80/pFM201 (U.S. Pat. No. 6,258,554), and the like.

Examples of parent strains which can be used to derive L-histidine-producing bacteria also include strains with increased expression of one or more genes encoding an L-histidine biosynthetic enzyme. Examples of such genes include the genes encoding ATP phosphoribosyltransferase (hisG), phosphoribosyl AMP cyclohydrolase (hisI), phosphoribosyl-ATP pyrophosphohydrolase (hisIE), phosphoribosyl-formimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

The L-histidine biosynthetic enzymes encoded by hisG and hisBHAFI are inhibited by L-histidine, and therefore the L-histidine-producing ability can also be efficiently enhanced by introducing a mutation into ATP phosphoribosyltransferase which imparts resistance to the feedback inhibition (Russian Patent Nos. 2003677 and 2119536).

Specific examples of strains having an L-histidine-producing ability include *E. coli* FERM-P-5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains which can be used to derive L-glutamic acid-producing bacteria include, but are not limited to, strains belonging to the genus *Escherichia*, such as *E. coli* VL334thrC⁺ (EP 1172433). *E. coli* VL334 (VKPM B-1641) is an L-isoleucine and L-threonine auxotrophic strain with mutations in the thrC and ilvA genes (U.S. Pat. No. 4,278,765). A wild-type allele of the thrC gene was transferred by general transduction using a bacteriophage P1 which was grown in wild-type *E. coli* K12 (VKPM B-7) cells. As a result, an L-isoleucine auxotrophic strain VL334thrC⁺ (VKPM B-8961), which is able to produce L-glutamic acid, was obtained.

Examples of parent strains which can be used to derive L-glutamic acid-producing bacteria include, but are not limited to, strains which are deficient in α-ketoglutarate dehydrogenase activity, or strains with increased expression of one or more genes encoding an L-glutamic acid biosynthetic enzyme. Examples of the genes involved in L-glutamic acid biosynthesis include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified to increase expression of the citrate synthetase gene, the phosphoenolpyruvate carboxylase gene, and/or the glutamate dehydrogenase gene include those disclosed in EP1078989A, EP955368A, and EP952221A.

Examples of strains which have been modified to reduce expression of the citrate synthetase gene and/or the phosphoenolpyruvate carboxylase gene, or are deficient in α-ketoglutarate dehydrogenase activity, include those disclosed in EP1078989A, EP955368A, and EP952221A.

Examples of parent strains which can be used to derive L-glutamic acid-producing bacteria also include strains with decreased or no activity of an enzyme that catalyzes synthesis of a compound other than L-glutamic acid which is produced via a biosynthetic pathway which branches off from the L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is obtained by disrupting the α-ketoglutarate dehydrogenase gene (also referred to as the "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in, or have reduced α-ketoglutarate dehydrogenase activity and can be obtained as described above. Such strains include *Pantoea ananatis* AJ13356. (U.S. Pat. No. 6,331, 419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645.

It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of the disruption of the αKGDH-E1 subunit gene (sucA). The above strain was identified as *Enterobacter agglomerans* when it was isolated, and was deposited as *Enterobacter agglomerans* AJ13356. However, it was recently re-classified as *Pantoea ananatis* on the basis of nucleotide sequencing of the 16S rRNA and so forth. Although AJ13356 was deposited at the aforementioned depository as *Enterobacter agglomerans*, for the purposes of this specification, it is described as *Pantoea ananatis*.

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407, 952). Also, as a parent strain, *E. coli* K-12 [W3110 (tyrA)/ pPHAB (FERM BP-3566), *E. coli* K-12 [W3110 (tyrA)/ pPHAD] (FERM BP-12659), *E. coli* K-12 [W3110 (tyrA)/ pPHATerm] (FERM BP-12662) and *E. coli* K-12 [W3110 (tyrA)/pBR-aroG4, pACMAB], also called AJ 12604 (FERM BP-3579) may be used (EP 488424 B1). Furthermore, L-phenylalanine producing *Escherichia* bacteria with enhanced activity of the protein encoded by the yedA or yddG genes may also be used (U.S. patent applications 2003/0148473 A1 and 2003/0157667 A1).

L-Tryptophan-Producing Bacteria

Examples of parent strains which can be used to derive L-tryptophan-producing bacteria include, but are not limited to, strains belonging to the genus *Escherichia*, such as *E. coli* JP4735/pMU3028 (DSM10122) and JP6015/pMU91 (DSM10123), which is deficient in tryptophanyl-tRNA synthetase encoded by a mutant trpS gene (U.S. Pat. No. 5,756, 345); *E. coli* SV164 (pGH5) having a serA allele encoding phosphoglycerate dehydrogenase not subject to feedback inhibition by serine and a trpE allele encoding anthranilate synthase not subject to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps with enhanced phosphoenolpyruvate-producing ability (WO9708333, U.S. Pat. No. 6,319,696), and the like, may be used. L-tryptophan-producing *Escherichia* bacteria with enhanced activity of the protein encoded by the yedA or yddG genes may also be used (U.S. patent applications 2003/0148473 A1 and 2003/ 0157667 A1).

Examples of parent strains which can be used to derive L-tryptophan-producing bacteria also include strains with enhanced activity of one of more enzymes such as anthranilate synthase, phosphoglycerate dehydrogenase, and tryptophan synthase. Anthranilate synthase and phosphoglycerate dehydrogenase are both subject to feedback inhibition by L-tryptophan and L-serine, so a mutation desensitizing the feedback inhibition may be introduced into these enzymes. Specific examples of strains having such a mutation include a *E. coli* SV164 which harbors desensitized anthranilate synthase, and a transformant strain obtained by introducing pGH5 (WO 94/08031) into *E. coli* SV164, which contains a mutant serA gene encoding feedback-desensitized phosphoglycerate dehydrogenase.

Examples of parent strains which can be used to derive L-tryptophan-producing bacteria also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing the expression of the gene which encodes tryptophan synthase, which is part of the tryptophan operon (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains which can be used to derive L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes include the proB gene coding for glutamate kinase desensitized to feedback inhibition by L-proline (DE Patent 3127361). In addition, the bacterium may be improved by enhancing the expression of one or more genes coding for proteins which promote secretion of L-amino acids from the bacterial cell. Such genes are exemplified by b2682 and b2683 (ygaZH genes) (EP1239041 A2).

Examples of bacteria belonging to the genus *Escherichia* which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application 2002/ 058315 A1) and its derivative strains with mutant N-acetylglutamate synthase (Russian Patent Application No. 2001112869), *E. coli* strain 382 (VKPM B-7926) (EP1170358A1), an arginine-producing strain with the argA gene encoding N-acetylglutamate synthetase (EP1170361A1), and the like.

Examples of parent strains which can be used to derive L-arginine producing bacteria also include strains with enhanced expression of one or more genes encoding an L-arginine biosynthetic enzyme. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Examples of parent strains which can be used to derive L-valine-producing bacteria include bacteria belonging to the genus *Escherichia* such as H-81 (VKPM B-8066), NRRL B-12287, and NRRL B-12288 (U.S. Pat. No. 4,391,907), VKPM B-4411 (U.S. Pat. No. 5,658,766), VKPM B-7707 (European patent application EP1016710A2), or the like.

Example of parent strains which can be used to derive L-valine-producing bacteria include, but are not limited to, strains which have been modified to overexpress the ilvGMEDA operon (U.S. Pat. No. 5,998,178). The region in the ilvGMEDA operon which is required for attenuation can be removed so that expression of the operon is not attenuated by the L-valine that is produced. Furthermore, the ilvA gene in the operon can be disrupted so that threonine deaminase activity is decreased.

Examples of parent strains which can be used to derive L-valine-producing bacteria also include strains with aminoacyl t-RNA synthetase mutants (U.S. Pat. No. 5,658,766). For example, *E. coli* VL1970, which has a mutation in the ileS gene, which encodes isoleucine tRNA synthetase, can be used. *E. coli* VL1970 was deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking $H^+$-ATPase can also be used as parent strains (WO96/06926).

L-Isoleucine-Producing Bacteria

Examples of parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Methods

The method for producing an L-amino acid includes the steps of cultivating a bacterium as described above in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

The medium used for culture may be either a synthetic or natural medium, so long as it includes a carbon source and a nitrogen source and minerals and, if necessary, appropriate amounts of nutrients which the bacterium requires for growth. Ethanol is used as the carbon source. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as by shaking and/or stirring with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, an 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting examples.

Example 1

Preparation of the *E. coli* Strain MG1655 Δtdh, rhtA*

The *E. coli* strain MG1655 Δtdh, rhtA* was constructed by inactivation of the native tdh gene encoding threonine dehydrogenase in *E. coli* MG1655 (ATCC 47076) using the cat gene, followed by introduction of the rhtA23 mutation which confers resistance to high concentrations of threonine (>40 mg/ml) and homoserine (>5 mg/ml).

To inactivate the native tdh gene, a DNA fragment carrying the chloramphenicol resistance marker ($Cm^R$) encoded by the cat gene was integrated into the chromosome of *E. coli* MG1655 (ATCC 700926) in place of the native gene by the method described by Datsenko K. A. and Wanner B. L. (Proc. Natl. Acad. Sci. USA, 2000, 97, 6640-6645) which is also called "Red-mediated integration" and/or "Red-driven integration". The recombinant plasmid pKD46 (Datsenko, K. A., Wanner, B. L., Proc. Natl. Acad. Sci. USA, 2000, 97, 6640-6645) with the thermo-sensitive replicon was used as the donor of the phage λ-derived genes responsible for the Red-mediated recombination system. *E. coli* BW25113 containing the recombinant plasmid pKD46 can be obtained from the *E. coli* Genetic Stock Center, Yale University, New Haven, USA, the accession number of which is CGSC7630.

A DNA fragment containing a $Cm^R$ marker encoded by the cat gene was obtained by PCR using the commercially available plasmid pACYC184 (GenBank/EMBL accession number X06403, "Fermentas", Lithuania) as the template, and primers P1 (SEQ ID NO: 3) and P2 (SEQ ID NO: 4). Primer P1 contains 35 nucleotides homologous to the 5'-region of the tdh gene introduced into the primer for further integration into the bacterial chromosome. Primer P2 contains 32 nucleotides homologous to the 3'-region of the tdh gene introduced into the primer for further integration into the bacterial chromosome.

PCR was provided using the "Gene Amp PCR System 2700" amplificatory (Applied Biosystems). The reaction mixture (total volume—50 µl) consisted of 5 µl of 10× PCR-buffer with 25 mM $MgCl_2$ ("Fermentas", Lithuania), 200 µM each of dNTP, 25 pmol each of the exploited primers and 1 U of Taq-polymerase ("Fermentas", Lithuania). Approximately 5 ng of the plasmid DNA was added to the reaction mixture as the template DNA for the PCR amplification. The temperature profile was the following: initial DNA denaturation for 5 min at 95° C., followed by 25 cycles of denaturation at 95° C. for 30 sec, annealing at 55° C. for 30 sec, elongation at 72° C. for 40 sec; and the final elongation for 5 min at 72° C. Then, the amplified DNA fragment was purified by agarose gel-electrophoresis, extracted using "GenElute Spin Columns" (Sigma, USA), and precipitated by ethanol.

The DNA fragment was used for electroporation and Red-mediated integration into the bacterial chromosome of the *E. coli* MG1655/pKD46.

MG1655/pKD46 cells were grown overnight at 30° C. in liquid LB-medium containing ampicillin (100 µg/ml), then diluted 1:100 with SOB-medium (Yeast extract, 5 g/l; NaCl, 0.5 g/l; Tryptone, 20 g/l; KCl, 2.5 mM; $MgCl_2$, 10 mM)

containing ampicillin (100 µg/ml) and L-arabinose (10 mM) (arabinose is used to induce the plasmid containing the genes of the Red system) and grown at 30° C. to reach an optical density of $OD_{600}$=0.4-0.7. The grown cells from 10 ml of the bacterial culture were washed 3 times with ice-cold de-ionized water, followed by suspension in 100 µl of the water. 10 µl of DNA fragment (100 ng) dissolved in the de-ionized water was added to the cell suspension. The electroporation was performed by a "Bio-Rad" electroporator (USA) (No. 165-2098, version 2-89) according to the manufacturer's instructions. Shocked cells were added to 1 ml of SOC medium (Sambrook et al, "Molecular Cloning A Laboratory Manual, Second Edition", Cold Spring Harbor Laboratory Press (1989)), incubated for 2 hours at 37° C., and then were spread onto L-agar containing 25 µg/ml of chloramphenicol. After 24 hours, colonies were tested for the presence of the $Cm^R$ marker in place of the native tdh gene by PCR using primers P3 (SEQ ID NO: 5) and P4 (SEQ ID NO: 6). For this purpose, a freshly isolated colony was suspended in 20 µl water, and then 1 µl of the suspension was used for PCR. The temperature profile follows: initial DNA denaturation for 5 min at 95° C.; then 30 cycles of denaturation at 95° C. for 30 sec, annealing at 55° C. for 30 sec and elongation at 72° C. for 30 sec; the final elongation for 5 min at 72° C. A few of the tested $Cm^R$ colonies contained the desired 1104 bp DNA fragment, confirming the presence of the $Cm^R$ marker DNA instead of the 1242 bp fragment of tdh gene. One of the strains was cured of the thermosensitive plasmid pKD46 by culturing at 37° C. and named E. coli MG1655Δtdh.

Then, the rhtA23 mutation from the VL614rhtA23 strain (Livshits V. A. et al, 2003, Res. Microbiol., 154:123-135) was introduced into MG1655 Δtdh, resulting in strain MG1655 Δtdh, rhtA*. The rhtA23 mutation confers resistance to high concentrations of threonine (>40 mg/ml) and homoserine (>5 mg/ml). For that purpose, the MG1655 Δtdh strain was infected with phage $P1_{vir}$ grown on the donor strain VL614rhtA23. The transductants were selected on M9 minimal medium containing 8 mg/ml homoserine and 0.4% glucose as the sole carbon source. Thus, the strain MG1655 Δtdh, rhtA* was constructed.

Example 2

Construction of the E. coli Strain MG1655::$P_{L-tac}$-adhE

The E. coli strain MG1655::$P_{L-tac}$adhE was obtained by replacing the native promoter region of the adhE gene encoding alcohol dehydrogenase E in the MG1655 strain with the $P_{L-tac}$ promoter.

To inactivate the native promoter region of the adhE gene, the DNA fragment carrying the $P_{L-tac}$ promoter and the chloramphenicol resistance marker ($Cm^R$) encoded by the cat gene was integrated into the chromosome of E. coli MG1655 in place of the native promoter region by the method described by Datsenko K. A. and Wanner B. L. (Proc. Natl. Acad. Sci. USA, 2000, 97, 6640-6645), which is also called "Red-mediated integration" and/or "Red-driven integration".

A fragment with the $P_{L-tac}$ promoter joined with the cat gene was obtained by PCR using chromosomal DNA of the E. coli strain MG1655$P_{L-tac}$xylE (WO2006/043730) as the template. The nucleotide sequence of the $P_{L-tac}$ promoter is presented in the Sequence listing (SEQ ID NO: 7). Primers P5 (SEQ ID NO: 8) and P6 (SEQ ID NO: 9) were used for the PCR amplification. Primer P5 contains 40 nucleotides which are complementary to the region which is located 318 bp upstream of the start codon of the adhE gene introduced into the primer, for further integration into the bacterial chromosome and the primer P6 contains 39 nucleotides which are identical to the 5'-sequence of the adhE gene.

PCR was provided using the "Gene Amp PCR System 2700" amplificatory (Applied Biosystems). The reaction mixture (total volume—50 µl) contained 5 µl of 10× PCR-buffer with 15 mM $MgCl_2$ ("Fermentas", Lithuania), 200 µM each of the dNTPs, 25 pmol each of the exploited primers, and 1 U of Taq-polymerase ("Fermentas", Lithuania). Approximately 20 ng of the E. coli MG1655$P_{L-tac}$xylE genomic DNA was added to the reaction mixtures as the template for PCR.

The temperature profile was the following: initial DNA denaturation for 5 min at 95° C., followed by 35 cycles of denaturation at 95° C. for 30 sec, annealing at 54° C. for 30 sec, elongation at 72° C. for 1.5 min and the final elongation for 5 min at 72° C. Then, the amplified DNA fragment was purified by agarose gel-electrophoresis, extracted using "GenElute Spin Columns" ("Sigma", USA), and precipitated by ethanol. The DNA fragment was used for electroporation and Red-mediated integration into the bacterial chromosome of the E. coli MG1655/pKD46.

MG1655/pKD46 cells were grown overnight at 30° C. in the liquid LB-medium containing ampicillin (100 µg/ml), then diluted 1:100 with SOB-medium (Yeast extract, 5 g/l; NaCl, 0.5 g/l; Tryptone, 20 g/l; KCl, 2.5 mM; $MgCl_2$, 10 mM) containing ampicillin (100 µg/ml) and L-arabinose (10 mM) (arabinose is used to induce the plasmid encoding genes of Red system) and grown at 30° C. to reach the optical density of $OD_{600}$=0.4-0.7. The grown cells from 10 ml of the bacterial culture were washed 3 times with ice-cold de-ionized water, followed by suspension in 100 µl of the water. 10 µl of the DNA fragment (100 ng) dissolved in the de-ionized water was added to the cell suspension. The electroporation was performed by a "Bio-Rad" electroporator (USA) (No. 165-2098, version 2-89) according to the manufacturer's instructions.

Shocked cells were added to 1-ml of SOC medium (Sambrook et al, "Molecular Cloning A Laboratory Manual, Second Edition", Cold Spring Harbor Laboratory Press (1989)), incubated for 2 hours at 37° C., and then spread onto L-agar containing 25 µg/ml of chloramphenicol.

About 100 clones were selected on M9 plates with 2% ethanol as the sole carbon source. Clones which grew on the M9 plates with 2% ethanol in 36 hours were chosen and tested for the presence of the $Cm^R$ marker in place of the native promoter region of the adhE gene by PCR using primers P7 (SEQ ID NO: 10) and P8 (SEQ ID NO: 11). For this purpose, a freshly isolated colony was suspended in 20 µl water and then 1 µl of the suspension was used for PCR. The temperature profile follows: initial DNA denaturation for 10 min at 95° C.; then 30 cycles of denaturation at 95° C. for 30 sec, annealing at 54° C. for 30 sec and elongation at 72° C. for 1.5 min; the final elongation for 1 min at 72° C. A few of the tested $Cm^R$ colonies contained the desired ~1800 bp DNA fragment, confirming the presence of the $Cm^R$ marker DNA in place of the 520 bp native promoter region of the adhE gene. One of the strains was cured of the thermo-sensitive plasmid pKD46 by culturing at 37° C. and named E. coli MG1655::$P_{L-tac}$-adhE.

Example 3

Construction of the E. coli Strain MG1655Δtdh, rhtA*, $P_{L\ tac}$adhE

The E. coli strain MG1655Δtdh, rhtA*, $P_{L-tac}$adhE was obtained by transduction of the $P_{L-tac}$ promoter from MG1655::$P_{L-tac}$adhE into MG1655Δtdh, rhtA*.

17

The MG1655 Δtdh, rhtA* was infected with phage P1$_{vir}$ grown on the donor strain MG1655::P$_{L-tac}$adhE, and MG1655Δtdh, rhtA*, P$_{L-tac}$adhE was obtained. This strain was checked for growth on M9 plates with 2% ethanol as the sole carbon source. The growth rate was the same as that for the strain MG1655::P$_{L-tac}$adhE.

Example 4

Construction of the E. coli Strain MG1655ΔadhE

This strain was constructed by inactivation of the native adhE gene in E. coli MG1655 by the kan gene.

To inactivate (or disrupt) the native adhE gene, a DNA fragment carrying the kanamycin resistance marker (Km$^R$) encoded by the kan gene was integrated into the chromosome of E. coli MG1655 (ATCC 700926) in place of the native gene by the method described by Datsenko K. A. and Wanner B. L. (Proc. Natl. Acad. Sci. USA, 2000, 97, 6640-6645) which is also called "Red-mediated integration" and/or "Red-driven integration".

A DNA fragment containing the Km$^R$ marker encoded by the kan gene was obtained by PCR using the commercially available plasmid pACYC177 (GenBank/EMBL accession number X06402, "Fermentas", Lithuania) as the template, and primers P9 (SEQ ID NO: 12) and P10 (SEQ ID NO: 13). Primer P9 contains 40 nucleotides which are homologous to the region which is located 318 bp upstream of the start codon of the adhE gene introduced into the primer for further integration into the bacterial chromosome. Primer P10 contains 41 nucleotides homologous to the 3'-region of the adhE gene introduced into the primer for further integration into the bacterial chromosome.

PCR was conducted using the "Gene Amp PCR System 2700" amplificatory (Applied Biosystems). The reaction mixture (total volume—50 µl) contained 5 µl of 10× PCR-buffer with 25 mM MgCl$_2$ ("Fermentas", Lithuania), 200 µM each of the dNTPs, 25 pmol each of the exploited primers, and 1 U of Taq-polymerase ("Fermentas", Lithuania). Approximately 5 ng of the plasmid DNA was added to the reaction mixture as the template DNA for the PCR amplification. The temperature profile was the following: initial DNA denaturation for 5 min at 95° C., followed by 25 cycles of denaturation at 95° C. for 30 sec, annealing at 55° C. for 30 sec, elongation at 72° C. for 40 sec; and the final elongation for 5 min at +72° C. Then, the amplified DNA fragment was purified by agarose gel-electrophoresis, extracted using "GenElute Spin Columns" ("Sigma", USA) and precipitated by ethanol.

The DNA fragment was used for electroporation and Red-mediated integration into the bacterial chromosome of the E. coli MG1655/pKD46.

MG1655/pKD46 cells were grown overnight at 30° C. in liquid LB-medium containing ampicillin (100 µg/ml), then diluted 1:100 with SOB-medium (Yeast extract, 5 g/l; NaCl, 0.5 g/l; Tryptone, 20 g/l; KCl, 2.5 mM; MgCl$_2$, 10 mM) containing ampicillin (100 µg/ml) and L-arabinose (10 mM) (arabinose is used to induce the plasmid encoding genes of Red system) and grown at 30° C. to reach an optical density of OD$_{600}$=0.4-0.7. The grown cells from 10 ml of the bacterial culture were washed 3 times by the ice-cold de-ionized water, followed by suspension in 100 µl of the water. 10 µl of DNA fragment (100 ng) dissolved in the de-ionized water was added to the cell suspension. The electroporation was performed by a "Bio-Rad" electroporator (USA) (No. 165-2098, version 2-89) according to the manufacturer's instructions.

18

Shocked cells were added to 1-ml of SOC medium (Sambrook et al, "Molecular Cloning A Laboratory Manual, Second Edition", Cold Spring Harbor Laboratory Press (1989)), incubated for 2 hours at 37° C., and then were spread onto L-agar containing 20 µg/ml of kanamycin. Colonies which grew within 24 hours were tested for the presence of Km$^R$ marker instead of the native adhE gene by PCR using primers P11 (SEQ ID NO: 14) and P12 (SEQ ID NO: 15). For this purpose, a freshly isolated colony was suspended in 20 µl water and then 1 µl of the suspension was used for PCR. The temperature profile follows: initial DNA denaturation for 5 min at 95° C.; then 30 cycles of denaturation at 95° C. for 30 sec, annealing at 55° C. for 30 sec and elongation at 72° C. for 30 sec; the final elongation for 5 min at 72° C. A few of the tested Km$^R$ colonies contained the desired ~1030 bp DNA fragment, confirming the presence of the Km$^R$ marker DNA in place of the 3135 bp fragment of adhE gene. One of the strains was cured of the thermosensitive plasmid pKD46 by culturing at 37° C. and was named E. coli MG1655ΔadhE.

Example 5

Construction of the E. coli Strain MG1655::P$_{L-tac}$-adhE*

The E. coli strain MG1655::P$_{L-tac}$ adhE* was obtained by introduction of a Glu568Lys (E568K) mutation (WO/2008/010565) into the adhE gene. At the first step, an 1.05 kbp fragment of the adhE gene carrying a E568K mutation was obtained by PCR using the genomic DNA of the E. coli strain MG1655 as the template and primers P13 (SEQ ID NO: 16) and P12 (SEQ ID NO: 15). Primer P15 is homologous to the 1662-1701 bp and 1703-1730 bp regions of the adhE gene, and includes the substitution of g/a (position 1702 bp) and primer P12 is homologous to the 3'-end of the adhE gene. PCR was conducted using the "Gene Amp PCR System 2700" amplificatory (Applied Biosystems). The reaction mixture (total volume—50 µl) contained 5 µl of 10× PCR-buffer with MgCl$_2$ ("TaKaRa", Japan), 250 µM each of the dNTPs, 25 pmol each of the exploited primers, and 2.5 U of Pyrobest DNA polymerase ("TaKaRa", Japan). Approximately 20 ng of the E. coli MG1655 genomic DNA was added to the reaction mixtures as the template for PCR. The temperature profile was the following: initial DNA denaturation for 5 min at 95° C., followed by 35 cycles of denaturation at 95° C. for 30 sec, annealing at 54° C. for 30 sec, elongation at 72° C. for 1 min and the final elongation for 5 min at 72° C. The fragment was purified by agarose gel-electrophoresis, and extracted using "GenElute Spin Columns" ("Sigma", USA) and precipitated with ethanol.

In the second step, a fragment containing the P$_{L-tac}$ promoter joined with the mutant adhE gene and marked by the cat gene, which provides chloramphenicol resistance, was obtained by PCR using the genomic DNA of the E. coli strain MG1655::P$_{L-tac}$adhE as the template (see Example 2), primer P11 (SEQ ID NO: 14), and a 1.05 kbp fragment carrying the mutant sequence (see above) as a second primer. Primer P11 is homologous to the region located at 402-425 bp, which is upstream of the start codon of the adhE gene. PCR was conducted using the "Gene Amp PCR System 2700" amplificatory (Applied Biosystems). The reaction mixture (total volume—50 µl) contained 5 µl of 10× PCR-buffer ("TaKaRa", Japan), 25 mM MgCl$_2$, 250 µM each of dNTP, 10 ng of the primer P11, 1 µg of the 1.05 kbp fragment as a second primer, and 2.5U of TaKaRaLA DNA polymerase ("TaKaRa", Japan). Approximately 20 ng of the E. coli MG1655::P$_{L-tac}$adhE genomic DNA was added to the reaction mixture as the template for PCR. The temperature profile was the following: initial DNA denaturation for 5 min at 95° C., followed by 35 cycles of denaturation at 95° C. for 30 sec, annealing at 54° C. for 30 sec, elongation at 72° C. for 3.5 min and the final elongation for 7 min at 72° C. The resulting fragment was purified by agarose gel-electrophoresis, extracted using "GenElute Spin Columns" ("Sigma", USA), and precipitated by ethanol.

To inactivate the native region of the adhE gene, a DNA fragment carrying the $P_{L-tac}$ promoter joined with the mutant adhE and chloramphenicol resistance marker ($Cm^R$) encoded by the cat gene (cat-$P_{L-tac}$adhE*, 4.7 kbp) was integrated into the chromosome of the E. coli MG1655ΔadhE by the method described by Datsenko K. A. and Wanner B. L. (Proc. Natl. Acad. Sci. USA, 2000, 97, 6640-6645) which is also called "Red-mediated integration" and/or "Red-driven integration". MG1655ΔadhE/pKD46 cells were grown overnight at 30° C. in liquid LB-medium containing ampicillin (100 μg/ml), then diluted 1:100 with SOB-medium (Yeast extract, 5 g/l; NaCl, 0.5 g/l; Tryptone, 20 g/l; KCl, 2.5 mM; $MgCl_2$, 10 mM) containing ampicillin (100 μg/ml) and L-arabinose (10 mM) (arabinose is used to induce the plasmid encoding the genes of the Red system) and grown at 30° C. to reach the optical density of $OD_{600}$=0.4-0.7. The grown cells from 10 ml of the bacterial culture were washed 3 times by the ice-cold de-ionized water, followed by suspension in 100 μl of the water. 10 μl of DNA fragment (300 ng) dissolved in the de-ionized water was added to the cell suspension. The electroporation was performed by a "Bio-Rad" electroporator (USA) (No. 165-2098, version 2-89) according to the manufacturer's instructions.

Shocked cells were added to 1-ml of SOC medium (Sambrook et al, "Molecular Cloning A Laboratory Manual, Second Edition", Cold Spring Harbor Laboratory Press (1989)), incubated for 2 hours at 37° C., and then spread onto L-agar containing 25 μg/ml of chloramphenicol.

The clones were selected on M9 plates with 2% ethanol as the sole carbon source.

The runaway clone was chosen and the full gene sequence was verified. The mutations were as follows: Glu568Lys (gag—aag), Ile554Ser (atc—agc), Glu22Gly (gaa—gga), Met236Val (atg—gtg), Ala786Val (gca—gta). This clone was named MG1655::$P_{L-tac}$adhE*.

Example 6

Construction of the E. coli Strain MG1655Δtdh, rhtA*, $P_{L-tac}$adhE*

The E. coli strain MG1655Δtdh, rhtA*, $P_{L-tac}$adhE* was obtained by transduction of the $P_{L-tac}$ adhE* mutation from the MG1655::$P_{L-tac}$adhE* strain.

The MG1655 Δtdh, rhtA* strain was infected with phage $P1_{vir}$ grown on the donor strain MG1655::$P_{L-tac}$adhE* and MG1655Δtdh, rhtA*, $P_{L-tac}$adhE* was obtained. This strain was checked for growth on M9 plates with 2% ethanol as the sole carbon source. The growth rate was the same as that for the strain MG1655::$P_{L-tac}$adhE*.

Example 7

Construction of the E. coli Strain MG1655 cat-$P_L$-ydbK

Modification of the regulator region of the ydbK gene, namely replacement of the native promoter region of the ydbK gene with the $P_L$ promoter, was constructed by the method first developed by Datsenko and Wanner (Proc. Natl. Acad. Sci. USA, 2000, 97(12), 6640-6645) called "Red-driven integration". According to this procedure, the PCR primers ydbK-attR (SEQ ID NO: 17) and PL-ydbK (SEQ ID NO:18) were constructed. Oligonucleotide ydbK-attR is homologous to the region upstream of the ydbK gene and the region adjacent to the gene conferring antibiotic resistance, which was present in the chromosomal DNA of BW25113 cat-$P_L$-yddG. Oligonucleotide PL-ydbK is homologous to both the region upstream of the start of ydbK and the region downstream to the $P_L$ promoter which was present in the chromosome of BW25113 cat-$P_L$-yddG. Obtaining BW25113 cat-$P_L$-yddG has been described in detail previously (EP1449918A1, RU2222596). The chromosomal DNA of strain BW25113 cat-$P_L$-yddG was used as the template for PCR. Conditions for PCR were the following: denaturation for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C. As a result, the PCR product was obtained, purified in agarose gel, and used for electroporation of E. coli MG1655/pKD46.

Electrocompetent cells were prepared as follows: E. coli strain MG1655 was grown overnight at 30° C. in LB medium containing ampicillin (100 mg/l), and the culture was diluted 100 times with 5 ml of SOB medium (Sambrook et al, "Molecular Cloning A Laboratory Manual, Second Edition", Cold Spring Harbor Laboratory Press (1989)) with ampicillin and L-arabinose (1 mM). The cells were grown with aeration at 30° C. to an $OD_{600}$ of ≈0.6 and then made electrocompetent by concentrating 100-fold and washing three times with ice-cold deionized $H_2O$. Electroporation was performed using 70 μl of cells and ≈100 ng of the PCR product. Following electroporation, the cells were incubated with 1 ml of SOC medium (Sambrook et al, "Molecular Cloning A Laboratory Manual, Second Edition", Cold Spring Harbor Laboratory Press (1989)) at 37° C. for 2.5 h, and then plated onto L-agar, and grown at 37° C. to select $Cm^R$ recombinants. Then, to eliminate the pKD46 plasmid, 2 passages on L-agar with Cm at 42° C. were performed and the colonies were tested for sensitivity to ampicillin. Thus, the E. coli strain MG1655 cat-$P_L$-ydbK was obtained.

Example 8

Construction of the Plasmid pP$_L$-ydbK3

The chromosome from the the MG1655 cat-$P_L$-ydbK strain was isolated by using the GenElute™ Bacterial Genomic DNA Kit. The chromosome and plasmid pMW119 were restricted by SalI endonuclease, mixed, and processed with T4 ligase under standard conditions ((Maniatis T., Fritsch E. E., Sambrook J. Molecular cloning. A laboratory manual. Cold Spring Harbor Laboratory). Then, the MG1655 strain was transformed with the ligation mixture, and Cm resistant derivatives were selected. The presence of the cat-$P_L$-ydbK construction was determined by PCR using plasmid DNA as the template and oligonucleotides ydbKC1(SEQ ID NO: 19) and ydbK CH2 (SEQ ID NO: 20) as primers. Thus, the plasmid pMW119 cat-$P_L$-ydbK big-1 was selected, which contained an insertion of 11.2 kb in length.

Furthermore, the plasmid pMW119 cat-$P_L$-ydbK big-1 was restricted by SmlI (SmoI) endonuclease and processed by Klenow fragment by a standard method (Maniatis T., Fritsch E. E., Sambrook J. Molecular cloning. A laboratory manual. Cold Spring Harbor Laboratory). The pMW119 plasmid was restricted by the SmaI endonuclease, and the plasmids were mixed and processed with T4 ligase under standard conditions. The ligation mixture was used to transform the MG1655 strain. Cm$^R$ clones were selected. Plasmids were isolated by the standard method of alkaline lysis and analyzed by BamHI restriction.

Thus, the plasmid pPLydbK3 (FIG. 1) was obtained. This plasmid contains the insertion cat-P$_L$-ydbK, which is 6.7 kb in length.

Example 9

The Effect of Enhancing Expression of the ydbK Gene on the Growth of E. coli

To evaluate the effect of enhancing expression of the ydbK gene on the growth of E. coli, the MG1655::P$_{L\text{-}tac}$adhE* strain was transformed with the plasmid pPLydbK3.

The strains MG1655::P$_{L\text{-}tac}$adhE* and MG1655::P$_{L\text{-}tac}$adhE* (pPLydbK3) were cultivated in test tubes in M9 minimal medium supplemented with 2% of ethanol and 25 mkg/ml Cm (for plasmid variant) at 37° C. with a rotary shaker. The growth curves of the strains are shown in FIG. 2.

As follows from FIG. 2, the MG1655::P$_{L\text{-}tac}$adhE* (pPLydbK3) strain grew better as compared to MG1655::P$_{L\text{-}tac}$adhE*.

Example 10

The Effect of Enhancing Expression of the ydbK Gene on L-Threonine Production

To evaluate the effect of enhancing expression of the ydbK gene on threonine production, the E. coli strain MG1655Δtdh, rhtA*, P$_{L\text{-}tac}$adhE* was transformed with the plasmid pVIC40 (the plasmid pVIC40 is described in detail in U.S. Pat. No. 5,705,371), then MG1655Δtdh, rhtA*, P$_{L\text{-}tac}$adhE* (pVIC40) was transformed with the plasmid pPLydbK3.

These strains, MG1655Δtdh, rhtA*, P$_{L\text{-}tac}$adhE* (pVIC40, pPLydbK3) and MG1655Δtdh, rhtA*, P$_{L\text{-}tac}$adhE* (pVIC40), were cultivated at 37° C. for 18 hours in a nutrient broth and 0.1 ml of each of the cultures was inoculated into 2 ml of fermentation medium in a 20×200 mm test tube, and cultivated at 32° C. for 72 hours with a rotary shaker. After cultivation for 48 hours and for 72 hours, the amount of L-threonine which had accumulated in the medium was determined by paper chromatography using the following mobile phase:butanol:acetic acid:water=4:1:1 (v/v). A solution 2% of ninhydrin in acetone was used as a visualizing reagent. A spot containing L-threonine was cut out, eluted in a 0.5% water solution of CdCl$_2$, and the amount of L-threonine was estimated spectrophotometrically at 540 nm. The results of 10 independent test tube fermentations are shown in Table 1.

TABLE 1

| Strain | 48 hr | | 72 hr | |
|---|---|---|---|---|
| | OD$_{550}$ | Thr, g/l | OD$_{550}$ | Thr, g/l |
| MG1655 Δtdh rhtA* cat-P$_{Ltac}$-adhE* (pVIC40) | 13.8 ± 0.5 | 2.4 ± 0.3 | 12.5 | 2.5 ± 0.2 |
| MG1655 Δtdh rhtA* cat-P$_{Ltac}$-adhE* (pVIC40, pPLydbK3) | 13.9 ± 0.7 | 3.8 ± 0.5 | 12.7 | 3.6 ± 0.5 |

As follows from Table 1, MG1655Δtdh, rhtA*, P$_{L\text{-}tac}$adhE* (pVIC40, pPLydbK3) produced a higher amount of L-threonine, as compared with MG1655Δtdh, rhtA*, P$_{L\text{-}tac}$adhE* (pVIC40).

Fermentation medium composition (g/l):

| Ethanol | 20 |
|---|---|
| (NH$_4$)$_2$SO$_4$ | 22 |
| K$_2$HPO$_4$ | 2 |
| MgSO$_4$•7H$_2$O | 0.8 |
| MnSO$_4$•5H$_2$O | 0.02 |
| FeSO$_4$•7H$_2$O | 0.02 |
| Thiamine hydrochloride | 0.002 |
| Yeast extract | 1.0 |
| CaCO$_3$ | 30 |

K$_2$HPO$_4$ and CaCO$_3$ were sterilized separately. The pH was adjusted to 7.0.

Example 11

Production of L-Lysine by E. coli AJ11442 P$_{l\text{-}tac}$adhE* (pPLydbK3)

To test the effect of enhancing expression of the ydbK gene on L-lysine production, at first, the L-lysine producing E. coli strain AJ11442 P$_{L\text{-}tac}$adhE* can be obtained by transferring DNA fragments from the chromosome of the above-described E. coli strain MG1655::P$_{L\text{-}tac}$adhE* to the L-lysine producing E. coli strain AJ11442 by P1 transduction. Then, the lysine-producing E. coli strain AJ11442 P$_{L\text{-}tac}$adhE* can be transformed with the plasmid pPLydbK3.

Both E. coli strains, AJ11442 P$_{L\text{-}tac}$adhE* and AJ11442 P$_{L\text{-}tac}$adhE* (pPLydbK3), can be cultured in L-medium containing streptomycin (20 mg/l) at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at an agitation speed of 115 rpm. After the cultivation, the amounts of L-lysine can be measured by a known method (Biotech-analyzer AS210 manufactured by Sakura Seiki Co.).

The composition of the fermentation medium (g/l) is as follows:

| Ethanol | 20 |
|---|---|
| (NH$_4$)$_2$SO$_4$ | 24 |
| K$_2$HPO$_4$ | 1.0 |
| MgSO$_4$7H$_2$O | 1.0 |
| FeSO$_4$7H$_2$O | 0.01 |
| MnSO$_4$5H$_2$O | 0.01 |
| Yeast extract | 2.0 |

The pH is adjusted to 7.0 by KOH and the medium is autoclaved at 115° C. for 10 min.
MgSO$_4$ 7H$_2$O is sterilized separately.
CaCO$_3$ is dry-heat sterilized at 180° C. for 2 hours and added to the medium for a final concentration of 30 g/l.

Example 12

Production of L-Cysteine by E. coli JM15(ydeD) P$_{l\text{-}tac}$adhE* (pPLydbK3)

To test the effect of enhancing expression of the ydbK gene on L-cysteine production, at first, the L-cysteine producing E. coli strain JM15(ydeD) P$_{l\text{-}tac}$adhE* can be obtained by transferring DNA fragments from the chromosome of the above-described E. coli strain MG1655::P$_{l\text{-}tac}$adhE* to the L-lysine producing E. coli strain JM15(ydeD) by P1 transduction. Then, the L-cysteine producing E. coli strain JM15(ydeD) P$_{l\text{-}tac}$adhE* can be transformed with the plasmid pPLydbK3.

E. coli JM15(ydeD) is a derivative of E. coli JM15 (U.S. Pat. No. 6,218,168) which can be transformed with DNA having the ydeD gene, which codes for a membrane protein, and is not involved in the biosynthetic pathway of any L-amino acid (U.S. Pat. No. 5,972,663). The strain JM15 (CGSC#5042) can be obtained from The Coli Genetic Stock Collection at the E. coli Genetic Resource Center, MCD Biology Department, Yale University (cgsc.biology.yale.edu/).

Fermentation conditions for evaluation of L-cysteine production were described in detail in Example 6 of U.S. Pat. No. 6,218,168 using ethanol as the carbon source instead of glucose.

Example 13

Production of L-Leucine by E. coli 57 $P_{l\text{-}tac}$adhE* (pPLydbK3)

To test the effect of enhancing expression of the ydbK gene on L-leucine production, at first, the L-leucine producing E. coli strain 57 $P_{l\text{-}tac}$adhE* can be obtained by transferring DNA fragments from the chromosome of the above-described E. coli strain MG1655::$P_{l\text{-}tac}$adhE* to the L-leucine producing E. coli strain 57 (U.S. Pat. No. 6,124,121)) by P1 transduction. Then, the E. coli L-leucine producing strain 57 $P_{l\text{-}tac}$adhE* can be transformed with the plasmid pPLydbK3. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both E. coli strains, 57 and 57(pPLydbK3), can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol—acetic acid—water=4:1:1).

The composition of the fermentation medium (g/l) (pH 7.2) is as follows:

| | |
|---|---|
| Ethanol | 20 |
| $(NH_4)_2SO_4$ | 25.0 |
| $K_2HPO_4$ | 2.0 |
| $MgSO_4\ 7H_2O$ | 1.0 |
| Thiamine | 0.01 |
| $CaCO_3$ | 25.0 |

$CaCO_3$ is sterilized separately.

Example 14

Production of L-Histidine by E. coli 80 $P_{l\text{-}tac}$adhE* (pPLydbK3)

To test the effect of enhancing expression of the ydbK gene on L-histidine production, at first, the L-histidine producing E. coli strain 80 $P_{l\text{-}tac}$adhE* can be obtained by transferring DNA fragments from the chromosome of the above-described E. coli strain MG1655::$P_{l\text{-}tac}$adhE* to the L-histidine producing E. coli strain 80 by P1 transduction. Then, the histidine-producing E. coli strain 80 $P_{l\text{-}tac}$adhE* can be transformed with the plasmid pPLydbK3. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VRPM B-7270 and then converted to a deposit under the Budapest Treaty on Jul. 12, 2004.

Both E. coli strains, 80 $P_{l\text{-}tac}$adhE* and 80 $P_{l\text{-}tac}$adhE* (pPLydbK3), can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Ethanol | 20 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4\ 7H_2O$ | 1.0 |
| $FeSO_4\ 7H_2O$ | 0.01 |
| $MnSO_4$ | 0.01 |
| Thiamine | 0.001 |
| Betaine | 2.0 |
| $CaCO_3$ | 60.0 |

Proline, betaine and $CaCO_3$ are sterilized separately.
The pH is adjusted to 6.0 before sterilization.

Example 15

Production of L-Glutamate by E. coli VL334thrC$^+$ $P_{l\text{-}tac}$adhE* (pPLydbK3)

To test the effect of enhancing expression of the ydbK gene on L-glutamate production, at first, the L-glutamate producing E. coli strain VL334thrC$^+$ $P_{l\text{-}tac}$adhE* can be obtained by transferring DNA fragments from the chromosome of the above-described E. coli strain MG1655::$P_{l\text{-}tac}$adhE* to the L-glutamate producing E. coli strain VL334thrC$^+$ (EP 1172433) by P1 transduction. Then, the E. coli L-glutamate-producing strain VL334thrC$^+$ $P_{l\text{-}tac}$adhE* can be transformed with the plasmid pPLydbK3. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number B-8961 and then converted to a deposit under the Budapest Treaty on Dec. 8, 2004.

Both strains, VL334thrC$^+$ $P_{l\text{-}tac}$adhE* and VL334thrC$^+$ $P_{l\text{-}tac}$adhE* (pPLydbK3), can be grown for 18-24 hours at 37° C. on L-agar plates. Then, one loop of the cells can be transferred into test tubes containing 2 ml of fermentation medium. The fermentation medium contains ethanol (20 g/l), ammonium sulfate (25 g/l), $KH_2PO_4$ (2 g/l), $MgSO_4$ (1 g/l), thiamine (0.1 mg/ml), L-isoleucine (70 μg/ml), and $CaCO_3$ (25 g/l). The pH is adjusted to 7.2. $CaCO_3$ is sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 16

Production of L-Phenylalanine by E. coli AJ12739 $P_{l\text{-}tac}$adhE* (pPLydbK3)

To test the effect of enhancing expression of the ydbK gene on L-phenylalanine production, at first, the L-phenylalanine producing E. coli strain AJ12739 $P_{l\text{-}tac}$adhE* can be obtained by transferring DNA fragments from the chromosome of the above-described E. coli strain MG1655::$P_{l\text{-}tac}$adhE* to the L-phenylalanine producing E. coli strain AJ12739 by P1 transduction. Then, the phenylalanine producing E. coli strain AJ12739 $P_{l\text{-}tac}$adhE* can be transformed with the plasmid pPLydbK3. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Both strains, AJ12739 $P_{l\text{-}tac}$adhE* (pPLydbK3) and AJ12739 $P_{l\text{-}tac}$adhE*, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Ethanol | 20 |
| $(NH_4)_2SO_4$ | 16.0 |
| $K_2HPO_4$ | 0.1 |
| $MgSO_4\,7H_2O$ | 1.0 |
| $FeSO_4\,7H_2O$ | 0.01 |
| $MnSO_4\,5H_2O$ | 0.01 |
| Thiamine HCl | 0.0002 |
| Yeast extract | 2.0 |
| Tyrosine | 0.125 |
| $CaCO_3$ | 20.0 |

Magnesium sulfate are sterilized separately.
$CaCO_3$ is dry-heat sterilized at 180° C. for 2 hours.
The pH is adjusted to 7.0.

Example 17

Production of L-Tryptophan by E. coli SV164 $P_{l\text{-}tac}$adhE* (pGH5, (pPLydbK3)

To test the effect of enhancing expression of the ydbK gene on L-tryptophan production, at first, the L-tryptophan producing E. coli strain SV164 $P_{l\text{-}tac}$adhE* (pGH5) can be obtained by transferring DNA fragments from the chromosome of the above-described E. coli strain MG1655::$P_{l\text{-}tac}$adhE* to the L-tryptophan producing E. coli strain SV164 (pGH5) by P1 transduction. Then, the tryptophan-producing E. coli strain SV164 $P_{l\text{-}tac}$adhE* (pGH5) can be transformed with the plasmid pPLydbK3. The strain SV164 has the trpE allele encoding anthranilate synthase not subject to feedback inhibition by tryptophan. The plasmid pGH5 harbors a mutant serA gene encoding phosphoglycerate dehydrogenase not subject to feedback inhibition by serine. The strain SV164 (pGH5) was described in detail in U.S. Pat. No. 6,180,373 or European patent 0662143.

Both strains, SV164 $P_{l\text{-}tac}$adhE* (pGH5, pPLydbK3) and SV164 $P_{l\text{-}tac}$adhE* (pGH5), can be cultivated with shaking at 37° C. for 18 hours in 3 ml of nutrient broth supplemented with tetracycline (20 mg/ml, marker of pGH5 plasmid). The cultures (0.3 ml each) can be inoculated into 3 ml of a fermentation medium containing tetracycline (20 mg/ml) in 20×200-mm test tubes, and cultivated at 37° C. for 48 hours with a rotary shaker at 250 rpm. After cultivation, the amount of tryptophan which accumulates in the medium can be determined by TLC as described in Example 16. The fermentation medium components are listed in Table 3, but should be sterilized in separate groups (A, B, C, D, E, F, and H), as shown, to avoid adverse interactions during sterilization.

TABLE 3

| Solutions | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Ethanol | 20.0 |
| | $MgSO_4\,7H_2O$ | 0.3 |
| C | $CaCl_2$ | 0.011 |
| D | $FeSO_4\,7H_2O$ | 0.075 |
| | Sodium citrate | 1.0 |
| E | $Na_2MoO_4\,2H_2O$ | 0.00015 |
| | $H_3BO_3$ | 0.0025 |
| | $CoCl_2\,6H_2O$ | 0.00007 |
| | $CuSO_4\,5H_2O$ | 0.00025 |
| | $MnCl_2\,4H_2O$ | 0.0016 |
| | $ZnSO_4\,7\,H_2O$ | 0.0003 |
| F | Thiamine HCl | 0.005 |
| G | $CaCO_3$ | 30.0 |
| H | Pyridoxine | 0.03 |

Solution A had a pH of 7.1, adjusted by $NH_4OH$.

Example 18

Production of L-Proline by E. coli 702ilvA $P_{l\text{-}tac}$adhE* (pPLydbK3)

To test the effect of enhancing expression of the ydbK gene on L-proline production, at first, the L-proline producing E. coli strain 702ilvA $P_{l\text{-}tac}$adhE* can be obtained by transferring DNA fragments from the chromosome of the above-described E. coli strain MG1655::$P_{l\text{-}tac}$adhE* to the L-proline producing E. coli strain 702ilvA by P1 transduction. Then, the proline-producing E. coli strain 702ilvA $P_{l\text{-}tac}$adhE* can be transformed with the plasmid pPLydbK3. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains, 702ilvA $P_{l\text{-}tac}$adhE* and 702ilvA $P_{l\text{-}tac}$adhE* (pPLydbK3), can be grown for 18-24 hours at 37°

C. on L-agar plates. Then, these strains can be cultivated under the same conditions as in Example 15.

Example 19

Production of L-Arginine by E. coli 382 P$_{l\text{-}tac}$adhE* (pPLydbK3)

To test the effect of enhancing expression of the ydbK gene on L-arginine production, at first the L-arginine producing *E. coli* strain 382 P$_{l\text{-}tac}$adhE* can be obtained by transferring DNA fragments from the chromosome of the above-described *E. coli* strain MG1655::P$_{l\text{-}tac}$adhE* to the L-arginine producing *E. coli* strain 382 by P1 transduction. Then, the arginine-producing *E. coli* strain 382 P$_{l\text{-}tac}$adhE* can be transformed with the plasmid pPLydbK3. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382 P$_{l\text{-}tac}$adhE* (pPLydbK3) and 382 P$_{l\text{-}tac}$adhE*, can be separately cultivated with shaking at 37° C. for 18 hours in 3 ml of nutrient broth, and 0.3 ml of the obtained cultures can be inoculated into 2 ml of a fermentation medium in 20×200-mm test tubes and cultivated at 32° C. for 48 hours on a rotary shaker.

After the cultivation, the amount of L-arginine which accumulates in the medium can be determined by paper chromatography using the following mobile phase:butanol:acetic acid:water=4:1:1 (v/v). A solution of ninhydrin (2%) in acetone can be used as a visualizing reagent. The spot containing L-arginine can be cut out, eluted with a 0.5% water solution of CdCl$_2$, and the amount of L-arginine can be estimated spectrophotometrically at 540 nm.

The composition of the fermentation medium (g/l) is as follows:

| | |
|---|---|
| Ethanol | 20 |
| (NH4)$_2$SO$_4$ | 35.0 |
| KH$_2$PO$_4$ | 2.0 |
| MgSO$_4$•7H$_2$O | 1.0 |
| Thiamine HCl | 0.0002 |
| Yeast extract | 1.0 |
| L-isoleucine | 0.1 |
| CaCO$_3$ | 5.0 |

Magnesium sulfate are sterilized separately.
CaCO$_3$ is dry-heat sterilized at 180° C. for 2 hours.
The pH is adjusted to 7.0.

Example 20

Production of L-Valine by E. coli H-81 P$_{L\text{-}tac}$adhE* (pPLydbK3)

To test the effect of enhancing expression of the ydbK gene on L-valine production, at first, the L-valine producing strain *E. coli* H-81 P$_{L\text{-}tac}$adhE* was obtained by transferring DNA fragments from the chromosome of the above-described *E. coli* strain MG1655::P$_{L\text{-}tac}$adhE* to the valine-producing *E. coli* strain H-81 (VKPM B-8066) by P1 transduction (Miller, J. H. Experiments in Molecular Genetics, Cold Spring Harbor Lab. Press, 1972, Plainview, N.Y.). Then, the strain *E. coli* H-81 P$_{L\text{-}tac}$adhE* was transformed with the plasmid pPLydbK3. The strain H-81 has been deposited in the Russian National Collection of Industrial Microorganisms (VKPM) (Russia 113545, Moscow, 1 Dorozhny proezd, 1) on Jan. 30, 2001 under accession number VKPM B-8066, and converted to an international deposit based on Budapest Treaty on Feb. 1, 2002.

The strains H-81 P$_{L\text{-}tac}$adhE* (pPLydbK3) and H-81 P$_{L\text{-}tac}$adhE* were cultivated at 37° C. for 18 hours in a nutrient broth and 0.1 ml of each of the cultures was inoculated into 2 ml of fermentation medium in a 20×200 mm test tube and cultivated at 32° C. for 72 hours with a rotary shaker. After cultivation for 48 hours and for 72 hours, the accumulated amounts of L-valine were measured by TLC as described in Example 16. The results of 10 independent test tube fermentations are shown in Table 2.

TABLE 2

| | 48 hr | | 72 hr | |
|---|---|---|---|---|
| Strain | OD$_{550}$ | Val, g/l | OD$_{550}$ | Val, g/l |
| H-81 P$_{Ltac}$-adhE* | 5.5 ± 0.5 | 1.1 ± 0.1 | 12.4 ± 0.6 | 1.6 ± 0.1 |
| H-81 P$_{Ltac}$-adhE* (pPLydbK3) | 16.8 ± 0.4 | 2.1 ± 0.2 | 16.1 ± 0.4 | 2.0 ± 0.1 |

As follows from Table 2, H-81 P$_{L\text{-}tac}$adhE* (pPLydbK3) produced a higher amount of L-valine, as compared with H-81 P$_{L\text{-}tac}$adhE*.

Fermentation medium composition (g/l):

| | |
|---|---|
| Ethanol | 20 |
| (NH$_4$)$_2$SO$_4$ | 15 |
| KH$_2$PO$_4$ | 1.5 |
| MgSO$_4$•7H$_2$O | 1 |
| Mameno (TN) | 0.4 |
| CaCO$_3$ | 25 |

CaCO$_3$ was dry-heat sterilized at 180° C. for 2 hours.
The pH was adjusted to 7.0.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing L-threonine and/or L-valine comprising:

cultivating an *Escherichia coli* which produces L-threonine and/or L-valine in a medium containing ethanol as the sole carbon source, and collecting said L-threonine and/or L-valine from the medium, wherein said *Escherichia coli* has been modified to enhance the expression of the ydbK gene.

2. The method according to claim 1, wherein said expression is enhanced by modifying an expression control sequence of the ydbK gene or by increasing the copy number of the ydbK gene.

3. The method according to claim 1, wherein said ydbK gene encodes a protein having a homology of not less than 95% with respect to the amino acid sequence shown in SEQ ID NO. 2.

4. The method according to claim 1, wherein said ydbK gene encodes a protein comprising the amino acid sequence shown in SEQ ID NO. 2.

* * * * *